(12) United States Patent
Auge, II et al.

(10) Patent No.: US 7,819,861 B2
(45) Date of Patent: *Oct. 26, 2010

(54) METHODS FOR ELECTROSURGICAL ELECTROLYSIS

(75) Inventors: Wayne K. Auge, II, Santa Fe, NM (US); Roy E. Morgan, San Jose, CA (US)

(73) Assignee: NuOrtho Surgical, Inc., Fall River, MA (US)

( * ) Notice: Subject to any disclaimer, the term of this patent is extended or adjusted under 35 U.S.C. 154(b) by 1326 days.

This patent is subject to a terminal disclaimer.

(21) Appl. No.: 11/010,174

(22) Filed: Dec. 10, 2004

(65) Prior Publication Data

US 2005/0182449 A1   Aug. 18, 2005
US 2010/0036446 A9   Feb. 11, 2010

Related U.S. Application Data

(63) Continuation of application No. PCT/US03/18575, filed on Jun. 10, 2003, and a continuation-in-part of application No. 11/006,079, filed on Dec. 6, 2004, which is a continuation-in-part of application No. PCT/US03/18116, filed on Jun. 6, 2003, application No. 11/010,174, which is a continuation-in-part of application No. 10/119,671, filed on Apr. 9, 2002, now Pat. No. 6,902,564, and a continuation-in-part of application No. 10/157,651, filed on May 28, 2002, now Pat. No. 7,066,932.

(60) Provisional application No. 60/387,775, filed on Jun. 10, 2002, provisional application No. 60/387,114, filed on Jun. 6, 2002, provisional application No. 60/387,775, filed on Jun. 10, 2002, provisional application No. 60/312,965, filed on Aug. 15, 2001, provisional application No. 60/293,809, filed on May 26, 2001.

(51) Int. Cl.
*A61B 18/14* (2006.01)

(52) U.S. Cl. .................. 606/32; 606/41; 606/45; 606/49

(58) Field of Classification Search ............... 607/100; 606/32, 41, 45, 49
See application file for complete search history.

(56) References Cited

U.S. PATENT DOCUMENTS 3,911,107 A   10/1975   Krezanoski (Continued)

FOREIGN PATENT DOCUMENTS

GB   2037920   7/1980

(Continued)

OTHER PUBLICATIONS

Babincova, Melina et al., "High-Gradient Magnetic Capture of Ferrofluids: Implications for Drug Targeting and Tumor Embolization", *Zeitschrift fur Naturforschung*, vol. 56-C 2001, 909-911.

(Continued)

*Primary Examiner*—Lee S Cohen
(74) *Attorney, Agent, or Firm*—Janeen Vilven; Vidal A. Oaxaca; Peacock Myers, P.C.

(57) ABSTRACT

Methods for electrosurgical electrolysis for treating tissue within a body, including methods that operate in an electrolyzable medium, including an aqueous electrolyzable medium, by means of electrolysis, and optionally by means of oxy-hydrogen combustion for use in treatment, including therapeutic methods of electrolysis to effect advantageous tissue changes.

30 Claims, 17 Drawing Sheets

U.S. PATENT DOCUMENTS

| | | |
|---|---|---|
| 3,941,135 A | 3/1976 | von Sturm et al. |
| 3,982,017 A | 9/1976 | Thiele |
| 4,014,777 A | 3/1977 | Brown |
| 4,105,017 A | 8/1978 | Ryaby et al. |
| 4,266,532 A | 5/1981 | Ryaby et al. |
| 4,266,533 A | 5/1981 | Ryaby et al. |
| 4,504,493 A | 3/1985 | Marshall et al. |
| 4,540,409 A | 9/1985 | Nystrom et al. |
| 4,615,347 A | 10/1986 | Schooley |
| 4,872,865 A | 10/1989 | Bloebaum et al. |
| 4,938,970 A | 7/1990 | Hustead et al. |
| 4,971,068 A | 11/1990 | Sahi |
| 5,014,699 A | 5/1991 | Pollack et al. |
| 5,236,456 A | 8/1993 | O'Leary et al. |
| 5,282,861 A | 2/1994 | Kaplan |
| 5,304,724 A | 4/1994 | Newton |
| 5,314,476 A | 5/1994 | Prewett et al. |
| 5,352,463 A | 10/1994 | Badylak et al. |
| 5,360,440 A | 11/1994 | Andersen |
| 5,366,443 A | 11/1994 | Eggers et al. |
| 5,403,825 A | 4/1995 | Lagarde et al. |
| 5,458,596 A | 10/1995 | Lax et al. |
| 5,494,538 A | 2/1996 | Kirillov et al. |
| 5,498,259 A | 3/1996 | Mourant et al. |
| 5,514,130 A | 5/1996 | Baker |
| 5,516,533 A | 5/1996 | Badylak et al. |
| 5,554,141 A | 9/1996 | Wendler |
| 5,569,242 A | 10/1996 | Lax et al. |
| 5,584,863 A | 12/1996 | Rauch et al. |
| 5,622,725 A | 4/1997 | Kross |
| 5,669,904 A | 9/1997 | Platt et al. |
| 5,669,907 A | 9/1997 | Platt et al. |
| 5,669,934 A | 9/1997 | Sawyer |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,741,261 A | 4/1998 | Moskovitz et al. |
| 5,746,896 A | 5/1998 | Shimamune et al. |
| 5,749,895 A | 5/1998 | Sawyer et al. |
| 5,788,976 A | 8/1998 | Bradford |
| 5,800,385 A | 9/1998 | Demopuls et al. |
| 5,820,583 A | 10/1998 | Demopulos et al. |
| 5,824,015 A | 10/1998 | Sawyer |
| 5,840,166 A | 11/1998 | Kaneko |
| 5,855,608 A | 1/1999 | Brekke |
| 5,860,950 A | 1/1999 | Demopulos et al. |
| 5,871,469 A | 2/1999 | Eggers et al. |
| 5,885,292 A | 3/1999 | Moskovitz et al. |
| 5,919,191 A | 7/1999 | Lennox et al. |
| 5,955,514 A | 9/1999 | Huang et al. |
| 5,964,968 A | 10/1999 | Kaneko |
| 6,032,077 A | 2/2000 | Pomeranz |
| 6,033,654 A | 3/2000 | Stedronsky et al. |
| 6,086,585 A | 7/2000 | Hovda et al. |
| 6,112,122 A | 8/2000 | Schwardt et al. |
| 6,117,109 A | 9/2000 | Eggers et al. |
| 6,135,998 A | 10/2000 | Palanker |
| 6,149,620 A | 11/2000 | Baker et al. |
| 6,159,194 A | 12/2000 | Eggers et al. |
| 6,162,219 A | 12/2000 | Nilsson et al. |
| 6,174,309 B1 | 1/2001 | Wrublewski et al. |
| 6,206,878 B1 | 3/2001 | Bishop et al. |
| 6,213,999 B1 | 4/2001 | Platt et al. |
| 6,214,003 B1 | 4/2001 | Morgan et al. |
| 6,224,592 B1 | 5/2001 | Eggers et al. |
| 6,235,024 B1 | 5/2001 | Tu |
| 6,241,723 B1 | 6/2001 | Heim et al. |
| 6,241,753 B1 | 6/2001 | Knowlton |
| 6,264,650 B1 | 7/2001 | Hovda et al. |
| 6,264,652 B1 | 7/2001 | Eggers et al. |
| 6,273,883 B1 | 8/2001 | Furumoto |
| 6,293,942 B1 | 9/2001 | Goble et al. |
| 6,306,134 B1 | 10/2001 | Goble et al. |
| 6,309,387 B1 | 10/2001 | Eggers et al. |
| 6,322,549 B1 | 11/2001 | Eggers et al. |
| 6,350,276 B1 | 2/2002 | Knowlton |
| 6,383,184 B1 | 5/2002 | Sharkey |
| 6,391,025 B1 | 5/2002 | Weinstein et al. |
| 6,416,509 B1 | 7/2002 | Goble et al. |
| 6,419,815 B1 | 7/2002 | Chambers |
| 6,461,352 B2 | 10/2002 | Morgan et al. |
| 6,463,336 B1 | 10/2002 | Mawhinney |
| 6,471,993 B1 | 10/2002 | Shastri et al. |
| 6,547,794 B2 | 4/2003 | Auge |
| 6,558,382 B2 | 5/2003 | Jahns et al. |
| 6,772,013 B1 | 8/2004 | Ingle et al. |
| 6,780,178 B2 * | 8/2004 | Palanker et al. ............... 606/34 |
| 6,824,555 B1 | 11/2004 | Towler et al. |
| 6,832,995 B1 | 12/2004 | Towler et al. |
| 6,890,332 B2 | 5/2005 | Truckai et al. |
| 6,902,564 B2 * | 6/2005 | Morgan et al. ................ 606/32 |
| 7,066,932 B1 | 6/2006 | Morgan et al. |
| 7,105,011 B2 | 9/2006 | Auge |
| 7,354,438 B2 | 4/2008 | Morgan et al. |
| 7,445,619 B2 | 11/2008 | Auge et al. |
| 7,549,989 B2 | 6/2009 | Morgan et al. |
| 2001/0007940 A1 | 7/2001 | Tu et al. |
| 2002/0165596 A1 | 11/2002 | Wilson |
| 2003/0028189 A1 | 2/2003 | Woloszko et al. |
| 2003/0216732 A1 | 11/2003 | Truckai et al. |
| 2003/0216733 A1 | 11/2003 | McClurken et al. |
| 2004/0167244 A1 | 8/2004 | Auge, II |
| 2004/0267255 A1 | 12/2004 | Auge, II et al. |
| 2005/0085806 A1 | 4/2005 | Auge, II et al. |
| 2009/0030410 A1 | 1/2009 | Auge, II et al. |
| 2009/0306645 A1 | 12/2009 | Morgan et al. |

FOREIGN PATENT DOCUMENTS

| | | |
|---|---|---|
| WO | WO02/102438 | 12/2002 |
| WO | WO03/015865 | 2/2003 |
| WO | WO03/103521 | 12/2003 |

OTHER PUBLICATIONS

Brennetot, R. et al., "Investigation of Chelate Formation, Intramoecular Energy Transfer and Luminescence Efficiency and Lifetimes in the Euthenoyltrifluoroacetone-trioctylphosphine oxide-Triton x-100 System Using Absorbance, Fluorescence and Photothermal Measurements", *Spectrochim ACTA A Mol. Biomol. Spectrosc., Part A-56* 2000 , 702-715.

Chen, S. S. et al., "Heat-Induced Changes in the Mechanics of a Collagenous Tissue: Isothermal, Isotonic Shrinkage", *Transactions of the ASME* vol. 120 1998 , 382-388.

Edwards, R B. et al., "Thermometric determination of cartilage matrix temperatures during thermal chondroplasty: comparison of bipolar and monopolar radiofrequency devices", *Arthroscopy Apr. 2002*;18(4) Apr. 2002 , 339-346.

Fink, Bernd et al., "Holmium: YAG Laser-Induced Aseptic Bone Necroses of the Femoral Condyle", *Arthroscopy: The Journal of Arthroscopic and Related Surgery* vol. 12 No. 2 1996 , 217-223.

Gould, Stephen E. et al., "Cellular Contribution of Bone Graft to Fusion", *Journal of Orthopaedic Research* vol. 18 2000 , 920-927.

Grant, Kyle M. et al., ""Magnetic Field-Controlled Microfluidic Transport"", *Journal of American Chemical Society (JACS) Articles*, vol. 124, No. 3 2002 , 462-467.

Ito, Takayasu et al., "Sensitivity of Osteoinductive Activity of Deminerlization and Defatted Rat Femur to Temperature and Duration of Heating", *Clinical Orthopaedics and Related Research* No. 316 1995 , 267-275.

Janzen, Dennis L. et al., "Osteonecrosis After Contact Neodymium: Yttrium Aluminum Garnet Arthroscopic Laser Meniscectomy", *AJR 169* 1997 , 855-858.

Lopez, Mandi J. et al., "Effects of Monopolar Radiofrequency Energy on Ovine Joint Capsular Mechanical Properties", *Clinical Orthopaedics and Related Research*, No. 374 2000, 286-297.

Medvecky, Michael J. et al., "Thermal Capsular Shrinkage: Basic Science and Clinical Applications", *Arthroscopy*, 2001, vol. 17, No. 6 Jul. 2001, 624-635.

Minczykowski, Andrzej et al., ""Effects of Magnetic Resonance Imaging on Polymorphonuclear Neutrophil Adhesion"", *Diagnostics and Medical Technolgy, Medical Science Monitor*, vol. 7(3) 2001, 482-488.

Mourant, Judith R. et al., "Improvements in Laser " Welding" of Chicken Bone Tibias in vitro", *Laser Sciences and Applications Group*, Los Alamos, NM, 1-8.

Mourant, Judith R. et al., "Laser Welding of Bone: Successful in vitro Experiments", *Laser Sciences and Applications Group*, Los Alamos, NM, 1-5.

Rozbruch, S. R. et al., "Osteonecrosis of the Knee Following Arthroscopic Laser Meniscectomy", *Arthroscopy: The Journal of Arthroscopic and Related Surgery* vol. 12 No. 2 1996, 245-250.

Thal, Raymond et al., "Delayed Articular Cartilage Slough: Two Cases Resulting From Holmium: YAG Laser Damage to Normal Articular Cartilage and a Review of the Literature", *Arthroscopy: The Journal of Arthroscopic and Related Surgery* vol. 12 No. 1 1996, 92-94.

Torchilin, Vladimir P., ""Drug Targeting"", *European Journal of Pharmaceutical Sciences*, vol. 11, Supplement 2 2000, S81-S91.

Wall, Michael S. et al., "Thermal Modification of Collagen", *J. Shoulder Elbow Surg.* vol. 8 No. 4 1999, 339-344.

Wallace, Andrew L. et al., "Electrothermal Shrinkage Reduces Laxity but Alters Creep Behavior in a Lapine Ligament Model", *J. Shoulder Elbow Surg.* vol. 10 No. 1 2001, 1-6.

Zhang, Min et al., ""Effects of the Demineralization Process on the Osteoinductivity of Demineralized Bone Matrix"", *J. Periodontaol*, vol. 68 No. 11 Nov. 1997, 1085-1092.

Zohar, Ofer et al., ""Thermal Imaging of Reeptor-Activated Heat Production in Single Cells"", *Biophysical Journal*, vol. 74 Jan. 1998, 82-89.

* cited by examiner

METHODS FOR ELECTROSURGICAL ELECTROLYSIS

CROSS-REFERENCE TO RELATED APPLICATIONS

This application is a continuation application of Patent Cooperation Treaty Application Ser. No. PCT/US03/18575, entitled Methods and Devices for Electrosurgical Electrolysis, filed on Jun. 10, 2003, which itself claims the benefit of the filing of U.S. Provisional Patent Application Ser. No. 60/387,775, entitled Methods and Devices for Electrosurgical Electrolysis, filed on Jun. 10, 2002; this application is a Continuation-in-Part of U.S. application Ser. No. 11/006,079 filed on Dec. 6, 2004, which itself is a Continuation-In-Part of: International Application No. PCT/US03/18116, filed Jun. 6, 2003, which claims the benefit of the filing of U.S. Provisional Patent Application Ser. No. 60/387,114, entitled Methods and Devices for Electrosurgery, filed on Jun. 6, 2002; this application is a continuation-in-part of U.S. application Ser. No. 11/006,079 which claims the benefit of the filing of U.S. Provisional Patent Application Ser. No. 60/387,775, entitled Methods and Devices for Electrosurgical Electrolysis, filed on Jun. 10, 2002; this application is a Continuation-In-Part of U.S. application Ser. No. 10/119,671 filed Apr. 9, 2002, now issued on Jun. 7, 2005 as U.S. Pat. No. 6,902,564 which itself claims the benefit of the filing of U.S. Provisional Patent Application Ser. No. 60/312,965, entitled System and Method of Electrosurgical Biologic Tissue Modification and Treatment Utilizing Oxy-Hydro Combustion-Acid base Shift Reactions, filed on Aug. 15, 2001; this Application is a Continuation-in-Part of U.S. patent application Ser. No. 10/157,651 filed on May 28, 2002, now issued on Jun. 27, 2006 as U.S. Pat. No. 7,066,932, which itself claims the benefit of the filing of U.S. Provisional Patent Application Ser. No. 60/293,809, entitled System and Method of Biologically Enhanced Irrigants in Surgical Procedures, filed on May 26, 2001; and the specification thereof of each of the foregoing is incorporated herein by reference.

BACKGROUND OF THE INVENTION

1. Field of the Invention (Technical Field)

The present invention relates to methods and devices for electrosurgical electrolysis, including devices that operate in an electrolyzable medium, including an aqueous electrolyzable medium, by means of electrolysis and optionally by means of oxy-hydrogen combustion, together with electrolyzable media for use in treatment and therapeutic methods of electrolysis to effect advantageous tissue changes.

2. Description of Related Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

Electrosurgical methods and devices are used in many medical treatment settings. However, the use of electrosurgical methods and devices designed to specifically induce antimicrobial activity and healing responses during surgical procedures, and particularly to induce antimicrobial activity and healing responses by means only of electrolysis, has not been previously disclosed.

Although the need for inducing antimicrobial activity and healing responses is clear, to help the host organism respond to pathogens more effectively and further natural healing responses, the use of electrosurgical methods and devices have not been utilized in this arena due to misconceptions in the prior art regarding the electrosurgical phenomenon. Prior art has limited electrosurgical applications to cutting, ablation, coagulation, vaporization, and the like due to contentions in the prior art regarding the mechanism of electrosurgical physiochemical action. It has been considered that electrosurgical procedures exert their effects via the generation of a plasma or related form of ionizing radiation. Accordingly, methods and devices disclosed in the prior art relate to treatment effects such as cutting, ablation, coagulation, and vaporization due to the effects of such purported ionizing radiation energy. Certainly, utilizing plasma or ionizing radiation to induce effects other than that of cutting, ablation, coagulation, and vaporization would not be and has not been conceived. Therefore, it has not been contemplated in the prior art that there are further uses of electrosurgical methods and devices, particularly those relating to antimicrobial or tissue healing effects due to electrolysis.

As disclosed in U.S. patent application Ser. No. 10/119,671, the electrosurgical process is governed by electrolysis and oxy-hydro combustion. This understanding allows for additional novel uses of electrosurgical methods and devices that have heretofore been unrecognized.

Disclosed herein are methods and devices designed to induce antimicrobial activity and healing responses during treatment procedures that utilize the understanding of the electrosurgical physiochemical process induced by the application of electromagnetic energy to the treatment locale, namely electrolysis and oxy-hydro combustion.

BRIEF SUMMARY OF THE INVENTION

In one embodiment the invention provides a device for localized electrolysis for use in treatment or therapy of a patient, and more particularly electrolysis of electrolytes, which electrolytes do not include tissues of the patient. The invention thus includes a device with a variable volume, designed such that at least a portion of the interior includes electrodes for electrolysis, and further designed such that at least one side of the interior is in fluidic contact with the area of the patient to be treated. The device can further include at least one fluidic passage for entry of fluids into the volume to serve as electrolytes. Such fluids can further include therapeutic agents. The invention further includes a device with at least one electrode included within a perforated housing, such that the electrode can be held in proximity to but not touching the tissue to be treated, thereby limiting electrolysis of the tissue to be treated. Such device can further include at least one fluidic passage for entry of fluids into the perforated housing to serve as electrolytes. Such fluids can further include therapeutic agents.

In another embodiment the invention provides methods for treatment or modification of tissues by means of locally induced electrolysis, which electrolysis does not include electrolysis of the tissues to be treated. The invention thus includes use of interfacing media or other materials that are applied to the tissues before, after or concurrently with the application of electromagnetic energy to induce electrolysis. The benefits of the electrolysis so produced can include local, in situ production of electrolyzed strong acid water for use as an anti-microbial agent, localized therapeutic heating of a site of trauma or tissue injury, oxygenation of tissues and, through use of any of a variety of agents concurrently administered, enhancement of host healing responses.

The invention further includes novel electrolysis interfacing media, including further including non-electrolyzable materials, which non-electrolyzable materials provide a matrix or structure, and optionally further provide therapeutic benefits.

Thus in one embodiment the invention provides an apparatus for electrosurgery, comprising: a probe with a distal end and a proximal end, with at least one active electrode and at least one return electrode disposed on the distal end, the proximal end forming a handle for holding the probe; an insulating sleeve positioned around the distal end of the probe; and an adjustably positionable actuator disposed on the handle and translatably connected to the insulating sleeve, such that the insulating sleeve can be longitudinally translated relative to the distal end of the probe, thereby forming a cavity of variable volume about the distal end of the probe. In this apparatus, the insulating sleeve can extend distally beyond the active electrode, such as extending distally between about 1 mm and about 40 mm beyond the active electrode. The apparatus can further comprise at least one detector proximal to the distal end of the probe and within the cavity of variable volume for detecting a parameter relating to electrolysis or oxy-hydro combustion. The detector can detect pH concentration or temperature. The detector can comprise a piezo-electric pyrometer, such as a thin-film piezo-electric pyrometer. In another embodiment, the detector detects temperature and comprises a thermo-luminescent crystal. In another embodiment, the detector can detect conductivity, ion concentrations, gas production, such as production of oxygen or hydrogen, gas consumption, such as consumption of oxygen or hydrogen, sound, such as sound at between about 10 kHz and about 600 kHz, or changes in local pressure. In the apparatus, the at least one detector can be disposed between the at least one active electrode and the at least one return electrode. The apparatus can further comprise a detection circuit for receiving a parameter detected by the at least one detector. The apparatus can also further comprise a control circuit providing an output control signal controlling an amount of power output to the at least one active electrode in response to an output from the detection circuit. In one embodiment of the apparatus, there is one active electrode, in another embodiment, there are at least two active electrodes. The at least one detector within the cavity, if provided, may be located within the cylindrical insulating sleeve. Thus the at least one detector proximal to the at least one active electrode can be located in front of the at least one active electrode. In the apparatus, the actuator can be a mechanical actuator or an electromechanical actuator. The actuator may be activated, thereby varying the volume of the cavity about the distal end of the probe, in response to a parameter relating to electrolysis detected by the detector. In this embodiment, the apparatus may further comprise a detection circuit for receiving a parameter detected by the detector, or a detection circuit for receiving a parameter detected by the detector and a control circuit providing an output control signal controlling the actuator in response to an output from the detection circuit. In the apparatus, the sleeve may be cylindrical.

In another embodiment, the invention provides an apparatus for electrosurgery, comprising: a probe with a distal end and a proximal end, the proximal end forming a handle for holding the probe; a translatable insulating luminal sleeve positioned around the distal end of the probe; an adjustably positionable actuator disposed on the handle and translatably connected to the insulating luminal sleeve, such that the insulating luminal sleeve can be longitudinally translated relative to the distal end of the probe, thereby forming a cavity of variable volume about the distal end of the probe; and at least one active electrode disposed on at least a portion of the interior of the insulating luminal sleeve. The insulating luminal sleeve may extend distally beyond the distal end of the probe, such as extending distally between about 1 mm and about 40 mm beyond the distal end of the probe. At least one return electrode may be disposed on the distal end of the probe. The at least one active electrode and the at least one return electrode may be located within the cavity of variable volume about the distal end of the probe. Alternatively, there may be provided at least one return electrode disposed on the insulating luminal sleeve. The apparatus may further comprise at least one detector proximal to the distal end of the probe and within the cavity of variable volume for detecting a parameter relating to electrolysis or oxy-hydro combustion. The detector may detect pH concentration, temperature, conductivity, ion concentrations, gas production, gas consumption, sound, or changes in local pressure. In one embodiment, the detector detects temperature and comprises a piezo-electric pyrometer, a thin-film piezo-electric pyrometer, or a thermo-luminescent crystal. In another embodiment, the detector detects the production or consumption of oxygen or hydrogen. In yet another embodiment, the detector detects sound at between about 10 kHz and about 600 kHz. In the apparatus, the at least one detector may be disposed between the at least one active electrode and the at least one return electrode. The apparatus may further comprise a detection circuit for receiving a parameter detected by the at least one detector, and optionally a control circuit providing an output control signal controlling an amount of power output to the at least one active electrode in response to an output from the detection circuit. The at least one detector within the cavity may be located within the insulating luminal sleeve. Alternatively, the at least one detector proximal to the distal end of the probe and within the cavity of variable volume may be located in front of the at least one active electrode. The actuator may be a mechanical actuator or an electromechanical actuator. In the apparatus, the actuator may be activated, thereby varying the volume of the cavity about the distal end of the probe, in response to a parameter relating to electrolysis detected by the detector. In this embodiment, the apparatus may further comprise a detection circuit for receiving a parameter detected by the detector, or a detection circuit for receiving a parameter detected by the detector and a control circuit providing an output control signal controlling the actuator in response to an output from the detection circuit. In the apparatus, the insulating luminal sleeve can be cylindrical, can be flexible, can be translucent, or can be transparent, and may be made from a polymeric material. Thus the insulating luminal sleeve may comprise glass, ceramic, alumina, zirconia, yttria, PETG, PTFE, nylon, PVC, ABS, polysulfone, polycarbonate, PEEK, polyamide, polyimide, or PMMA. The apparatus may further comprise a power supply in electrical communication with the at least one active electrode, which power supply may be an alternating current power supply, or a direct current power supply, and may optionally provide a source of radiofrequency energy.

In yet another embodiment, the invention provides an apparatus for electrosurgery, comprising: a probe body with a distal end and a proximal end, the proximal end forming a handle for holding the probe; a flexible insulating luminal sleeve positioned around the distal end of the probe; an adjustably positionable actuator disposed on the handle and translatably connected to the insulating luminal sleeve, such that the insulating luminal sleeve can be longitudinally translated relative to the distal end of the probe, thereby forming a cavity of variable volume about the distal end of the probe; and at least one active electrode disposed on at least a portion of the interior of the insulating luminal sleeve. In the apparatus, the flexible insulating luminal sleeve may be bell shaped, whereby the distal end of the flexible insulating luminal sleeve has a diameter greater than the diameter of the proximal end of the flexible insulating luminal sleeve. The insulating sleeve may extend distally between about 1 mm and about 40 mm beyond the distal end of the probe. At least one return electrode may be disposed on the distal end of the probe, such as either located within the cavity of variable volume about the distal end of the probe or on the flexible insulating luminal sleeve. The at least one active electrode may be flexible, and may comprise a semi-conductive doped polymeric material. Alternatively, the at least one active electrode may comprise a metallic conductive paint, a metallic based conductive adhesive, a plasma vapor deposited metal, a chemical vapor deposited metal, a thin-film metallic leaf, or a conductively doped substrate. The apparatus may further comprise at least one detector proximal on the distal end of the probe and within the cavity of variable volume for detecting a parameter relating to electrolysis or oxy-hydro combustion, such as a detector that detects pH concentration, temperature, conductivity, ion concentrations, gas production, gas consumption, sound, or changes in local pressure. The detector may detect temperature and comprise a piezo-electric pyrometer, a thin-film piezo-electric pyrometer, or a thermo-luminescent crystal. Alternatively, the detector may detect the production or consumption of oxygen or hydrogen, or may detect sound at between about 10 kHz and about 600 kHz. The at least one detector may be disposed between the at least one active electrode and the at least one return electrode. The apparatus may further comprise a detection circuit for receiving a parameter detected by the at least one detector, and optimally a control circuit providing an output control signal controlling an amount of power output to the at least one active electrode in response to an output from the detection circuit. The at least one detector within the cavity may be located within the insulating luminal sleeve. Alternatively, the at least one detector on the distal end of the probe and within the cavity of variable volume may be located distal of the at least one active electrode. The actuator may be a mechanical actuator or an electro-mechanical actuator, and the actuator may be activated, thereby varying the volume of the cavity about the distal end of the probe, in response to a parameter relating to electrolysis detected by the detector. The apparatus may include a detection circuit for receiving a parameter detected by the detector, and optionally a control circuit providing an output control signal controlling the actuator in response to an output from the detection circuit. The insulating luminal sleeve may be cylindrical, translucent, or transparent, and may be made from a polymeric material. Thus the insulating luminal sleeve may comprise a silicone rubber, a polyimide, a fluoro-polymer, a polyester, a polyethylene, a polyurethane, a poly-vinyl chloride, a co-polymer of the foregoing, a tertiary co-polymer of the foregoing or a woven fabric of the foregoing. The apparatus may further comprise a power supply in electrical communication with the at least one active electrode, which may be an alternating current power supply, or a direct current power supply, and may optimally provide a source of radiofrequency energy.

In yet another embodiment, there is provided an apparatus for electrosurgery, comprising: a probe body with a distal end and a proximal end, the proximal end forming a handle for holding the probe; a flexible insulating extension extending from the distal end of the probe; and at least one active electrode disposed on the flexible insulating extension. The flexible insulating extension may extend between about 1 mm and about 40 mm beyond the distal end of the probe body. There may be provided at least one return electrode disposed on the distal end of the probe body. The at least one active electrode may be flexible, and may comprise a semi-conductive polymeric material. Thus the at least one active electrode may comprise a metallic conductive paint, a metallic based conductive adhesive, a plasma vapor deposited metal, a chemical vapor deposited metal, a thin-film metallic leaf, or a conductively doped substrate. The flexible insulating extension may be cylindrical, optionally with the at least one active electrode disposed on the interior cylinder wall of the cylindrical flexible insulating extension. The flexible insulating extension may also be translucent or transparent. The flexible insulating extension may be made from a polymeric material, and may include a silicone rubber, a polyimide, a fluoro-polymer, a polyester, a polyethylene, a polyurethane, a poly-vinyl chloride, a co-polymer of the foregoing, a tertiary co-polymer of the foregoing or a woven fabric of the foregoing. The apparatus may further comprise a power supply in electrical communication with the at least one active electrode. The power supply may be an alternating current power supply or a direct current power supply, and may optionally provide a source of radiofrequency energy. The at least one active electrode can comprise a conductive polymer on at least one surface of the flexible insulating extension, such as wherein the at least one active electrode surface area is defined by a non-conductive mask over at least one portion of the conductive doped polymer. The non-conductive mask may comprise a silicone rubber, a polyimide, a fluoro-polymer, a polyester, a polyethylene, a polyurethane, a poly-vinyl chloride, a co-polymer of the foregoing, a tertiary co-polymer of the foregoing or a woven fabric of the foregoing.

In yet another embodiment, there is provided an apparatus for electrosurgery of an anatomical structure within a body, comprising: a probe body with a distal end and a proximal end, the proximal end forming a handle for holding the probe body; a flexible insulating luminal sleeve positioned around the distal end of the probe body; an adjustably positionable actuator disposed on the handle and translatably connected to the insulating luminal sleeve, such that the insulating luminal sleeve can be longitudinally translated relative to the distal end of the probe body, thereby forming a cavity of variable volume and dimension about the distal end of the probe body; and at least one active electrode disposed on at least a portion of the interior of the insulating luminal sleeve. The flexible insulating luminal sleeve may be bell shaped, whereby the distal end of the flexible insulating luminal sleeve has a diameter greater than the diameter of the proximal end of the flexible insulating luminal sleeve. The distal diameter of the flexible insulating luminal sleeve may increase as the insulated luminal sleeve is longitudinally translated relative to the distal end of the probe body. In the apparatus, the insulating sleeve may extend distally between about 1 mm and about 40 mm beyond the distal end of the probe. In the apparatus, there may be provided at least one return electrode disposed on the distal end of the probe body, such as wherein the at least one return electrode is located within the cavity of variable volume and dimension about the distal end of the probe body. The apparatus may further comprise at least one return electrode disposed on the flexible insulating luminal sleeve. In any embodiment, the at least one active electrode may be flexible, and may comprise a semi-conductive polymeric material, or may comprise a metallic conductive paint, a metallic based conductive adhesive, a plasma vapor deposited metal, a chemical vapor deposited metal, a thin-film metallic leaf, or a conductively doped substrate. The apparatus may further comprise at least one detector proximal on the distal end of the probe and within the cavity of variable volume and dimension for detecting a parameter relating to electrolysis or oxy-hydro combustion, such as a detector which detects pH concentration, temperature, conductivity, ion concentrations, gas production, gas consumption, sound, or changes in local pressure. In one embodiment, the detector may detect temperature and comprise a piezo-electric pyrometer, a thin-film piezo-electric pyrometer, or a thermo-luminescent crystal. Alternatively, the detector may detect the production or consumption of oxygen or hydrogen or may detect sound at between about 10 kHz and about 600 kHz. The at least one detector may be disposed between the at least one active electrode and the at least one return electrode. The apparatus may further comprise a detection circuit for receiving a parameter detected by the at least one detector, and optionally may further comprise a control circuit providing an output control signal controlling an amount of power output to the at least one active electrode in response to an output from the detection circuit. In the apparatus, the at least one detector within the cavity may be located within the insulating luminal sleeve, such as located in front of the at least one active electrode. In the apparatus, the actuator may be a mechanical actuator or an electro-mechanical actuator, optionally wherein the actuator is activated, thereby varying the volume and dimension of the cavity about the distal end of the probe, in response to a parameter relating to electrolysis detected by the detector. The apparatus may further comprise a detection circuit for receiving a parameter detected by the detector, or a detection circuit for receiving a parameter detected by the detector and a control circuit providing an output control signal controlling the actuator in response to an output from the detection circuit. In the apparatus, the flexible insulating luminal sleeve may be cylindrical, and may further be translucent or transparent. The flexible insulating luminal sleeve may be made from a polymeric material, and may comprise a silicone rubber, a polyimide, a fluoro-polymer, a polyester, a polyethylene, a polyurethane, a poly-vinyl chloride, a co-polymer of the foregoing, a tertiary co-polymer of the foregoing or a woven fabric of the foregoing. In the apparatus, the flexible insulating luminal sleeve can be conformed to the shape of an anatomical structure within a body by longitudinal translation of the flexible insulating luminal sleeve, thereby varying at least one dimension of the flexible insulating luminal sleeve. In another embodiment, the flexible insulating luminal sleeve can further comprise a shape memory alloy, such as an expanded shape formed by a support structure of the shape memory alloy. The apparatus may further comprise a power supply in electrical communication with the at least one active electrode, which power supply may be an alternating current power supply or a direct current power supply, and optionally may provide a source of radiofrequency energy.

It may thus be seen that the invention includes a method for treating tissue within the body, comprising: providing a probe with a distal end and a proximal end, with at least one active electrode disposed on the distal end; positioning the at least one active electrode adjacent the tissue to be treated; providing an electrolyzable interfacing medium adjacent the at least one active electrode; and, providing sufficient electrical energy to the at least one active electrode to induce electrolysis of the electrolyzable interfacing medium without inducing combustion of the products of electrolysis or formation of a plasma.

Alternatively, the invention includes a method for treating tissue within the body, comprising: providing a probe with a distal end and a proximal end and a flexible insulating extension extending from the distal end of the probe, with at least one active electrode disposed on the flexible insulating extension; positioning the at least one active electrode adjacent the tissue to be treated; providing an electrolyzable interfacing medium adjacent the at least one active electrode; and, providing sufficient electrical energy to the at least one active electrode to induce electrolysis of the electrolyzable interfacing medium without inducing combustion of the products of electrolysis or formation of a plasma.

Alternatively, the invention provides a method for treating tissue within the body, comprising: providing a probe with a distal end and a proximal end, with the distal end comprising a cavity wherein is disposed at least one active electrode; positioning the cavity adjacent the tissue to be treated; providing an electrolyzable interfacing medium adjacent the at least one active electrode; and, providing sufficient electrical energy to the at least one active electrode to induce electrolysis of the electrolyzable interfacing medium without inducing combustion of the products of electrolysis or formation of a plasma.

In yet another alternative, the invention provides a method for treating tissue within the body, comprising: providing a probe with a distal end and a proximal end, with the distal end comprising a variable volume cavity wherein is disposed at least one active electrode; positioning the cavity adjacent the tissue to be treated; providing an electrolyzable interfacing medium adjacent the at least one active electrode; and, providing sufficient electrical energy to the at least one active electrode to induce electrolysis of the electrolyzable interfacing medium without inducing combustion of the products of electrolysis or formation of a plasma. In this method, it may be provided to vary the volume of the cavity.

In all the foregoing methods, the electrolyzable interfacing medium may comprise a hydrogel, a sol-gel, a wax, or a liquid. The electrolyzable interfacing medium may lubriciously soften in response to electrolysis. The electrolyzable interfacing medium may comprise an adhesive. The electrolyzable interfacing medium may also comprise a therapeutically effective agent, such as an antiseptic, growth factor, or apoptotic agent. In all the foregoing methods, the electrolyzable interfacing medium may effect a change in pH on electrolysis, may effect a change in impedance on electrolysis, or may effect a change in net electrical potential on electrolysis. In the methods, upon electrolysis the electrolyzable interfacing medium may form one or more chemical gradients or a thermal gradient. In all the foregoing methods, the electrolyzable interfacing medium may be provided by disposing within the probe prior to positioning the probe. Byproducts of electrolysis generated within the cavity may be controlled to effect the desired result. The methods may further comprise the step of detecting at least one byproduct of electrolysis within the cavity, such as pH concentration, temperature, conductivity, ion concentrations, gas production, gas consumption, sound, or changes in local pressure.

The invention further provides a method for treating tissue within the body, comprising: providing a non-electrolyzable material in combination with an electrolyzable interfacing medium adjacent the tissue to be treated; and applying sufficient electrical energy to induce electrolysis of the electrolyzable interfacing medium without inducing combustion of the products of electrolysis or formation of a plasma. In this method, the non-electrolyzable material may provide sufficient structure to at least partially contain the electrolyzable interfacing medium. Alternatively, the non-electrolyzable material may form a shell upon electrolysis of the electrolyzable interfacing medium, thereby at least partially containing the electrolyzable interfacing medium. In yet another alternative, the non-electrolyzable material may be interstitially disposed within voids of the tissue to be treated, forming an adhesive and hardened structure upon electrolysis of the of the electrolyzable interfacing medium, such as wherein the tissue to be treated is a bone, and wherein at least one void therein is a fracture surface. In this aspect, the non-electrolyzable material in combination with an electrolyzable interfacing medium may further comprise an osteo-inductive, osteo-conductive or osteogenic agent. The non-electrolyzable material may comprise a porous co-polymer of polyglycolic acid or polylactic acid, a collagen network, demineralized bone matrix, calcium phosphate cement, tricalcium phosphate, hydroxyapatite, non-collagenous protein, bioactive glass, tantalum or combinations of the foregoing. The electrolyzable interfacing medium may further comprise a liquid, a gel, a sol-gel, a wax or a solid.

In yet another alternative embodiment, there is provided a method for treating tissue within the body, comprising: providing an aqueous electrolyzable interfacing medium adjacent the tissue to be treated; and applying sufficient electrical energy to induce electrolysis of the electrolyzable interfacing medium without inducing combustion of the products of electrolysis or formation of a plasma, whereby acidic electrolyzed water is generated adjacent the tissue to provide a therapeutic effect. In this method, the electrical energy may be direct current. The electrical energy to induce electrolysis may be delivered by means of an active electrode adjacent to but not in contact with the tissue to be treated. The active electrode may be in fluid communication with the tissue to be treated but disposed within a structure preventing contact of the active electrode with the tissue to be treated. The structure may comprise a cavity or a porous structure.

In yet another embodiment, the invention provides a wound dressing for effecting electrolysis, comprising: a flexible thin film with a top surface and a bottom wound contacting surface comprising at least one first electrically conductive surface and at least one second electrically conductive surface; a conductive and electrolyzable interfacing medium contacting the at least one first electrically conductive surface; and, a source of electrical energy in electrical communication with the at least one first electrically conductive surface, thereby forming an active electrode, and with the at least one second electrically conductive surface, thereby forming a return electrode, whereby the conductive and electrolyzable interfacing medium completes an electrochemical electrolysis circuit when wetted by bodily fluids or an interfacing medium. In the wound dressing, the source of electrical energy may be a battery, such as a battery disposed on the top surface of the flexible thin film. Alternatively, in the wound dressing, the source of electrical energy may be a photovoltaic cell, such as a photovoltaic cell disposed on the top surface of the flexible thin film. In one embodiment, the top surface of the flexible thin film comprises the photovoltaic cell. In the wound dressing, the conductive and electrolyzable interfacing medium may be crystalline. The wound dressing may also further comprise an adhesive for fixing the flexible thin film on a wound. The wound dressing may also further comprise a passive current limiting circuit.

In yet another embodiment, the invention provides a method for treating tissue within the body, comprising: providing an aqueous electrolyzable interfacing medium adjacent the tissue to be treated; providing a variable volume structure containing an active electrode; applying sufficient electrical energy to the active electrode to induce electrolysis of the electrolyzable interfacing medium without inducing combustion of the products of electrolysis or formation of a plasma, whereby acidic electrolyzed water is generated adjacent the tissue to provide a therapeutic effect. The electrical energy may be direct current. In the method, the electrolysis may result in the formation of elemental gases adjacent the tissue to be treated. The variable volume structure may comprise a cavity or a porous structure.

In yet another embodiment, the invention provides a method for treating tissue within the body, comprising: providing an aqueous electrolyzable interfacing medium adjacent the tissue to be treated; providing an active electrode contained within a structure, the active electrode being in fluid contact with the tissue to be treated but spaced by the structure a determinable distance from the tissue to be treated; applying sufficient electrical energy to the active electrode to induce electrolysis of the electrolyzable interfacing medium without inducing combustion of the products of electrolysis or formation of a plasma, whereby acid base pairs are generated in the medium adjacent the tissue to provide a therapeutic effect. In this method, the structure may comprise a cavity or a porous structure.

A primary object of the present invention is to provide devices and methods relating to electrosurgical electrolysis (sometimes called electrolytic electrosurgery herein).

Another object is to provide variable chamber devices for electrosurgical electrolysis.

Another object is to devices, including an active electrode and a return electrode, for use in electrosurgical electrolysis.

Another object is to provide a cavity or chamber wherein the active electrode of an electrosurgical electrolysis probe is disposed.

Another object is to provide variable volume cavities or chambers on probes, preferably wherein the active electrode is disposed, for use in electrosurgical electrolysis.

Yet another object of the invention is to provide a variety of electrolytic media for use in electrosurgical electrolysis.

Yet another object of the invention is to provide a variety of electrolytic media, including one or more substrates, for use in electrosurgical electrolysis.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1A:
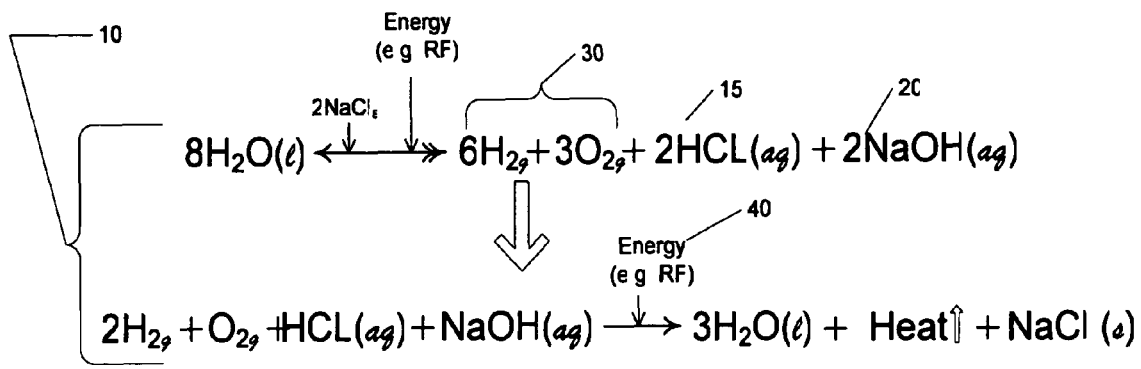
FIG. 1A is the stoichiometric chemical equation for chemical reactions related to the invention and known to govern the electrosurgical process.

The equations of FIG. 1A illustrate the chemical equations that describe the overall electrolysis and oxy-hydro reaction, with associated acid-base shifts, resulting from electrolysis of water and subsequent ignition of the resulting oxygen and hydrogen. The physiochemistry of the electrosurgical process consists of an acid-base shift that governs the relative availability of the amount of water that can be consumed as part of an electrolysis chemical reaction. The electrolysis reaction is driven by the high frequency current flowing between active and return electrodes in both the bi-polar and mono-polar modes of operation of electrosurgical probes. This electrolysis and oxy-hydro combustion theory accounts for all necessary chemical and energy constituents that are present as well as the physical observations of light emission and heat generation during the use of such devices. The physiochemical occurrences of electrosurgery have been reconciled into a single accurate and cohesive theory.

Chemical equations 10 generally govern the process herein disclosed, whereby the initial liberation of elemental oxygen and hydrogen gases 30 occurs by means of electrolysis. Given that the underwater electrosurgical process often occurs in a salt solution, either applied or that of the tissue or cell itself, such as a 0.9% by weight saline solution, the true role of these elements should be reconciled. The presence and true action of the salt, i.e. sodium chloride (NaCl) for example, can be accounted for by means of equations 10. The normal stoichiometry of the electrolysis reaction dictates that if elemental gas separation is occurring, then the solute participants must join with the remaining solution components of water to form a complementary acid-base pair. This pair is shown on the right-hand side of the upper half of equations 10 as hydrochloric acid 15 and sodium hydroxide 20 base pair. As is well known, hydrogen and oxygen gases 30 can be co-mingled without spontaneous exothermic reaction. A small amount of energy, such as RF energy 40, is required to overcome the nominally endothermic reaction and ignite the oxy-hydro combustion. Once ignited, the reaction will continue until all the reactants are consumed and reduced to the products shown on the right-hand side of the lower half of equations 10.

Figure 1B:
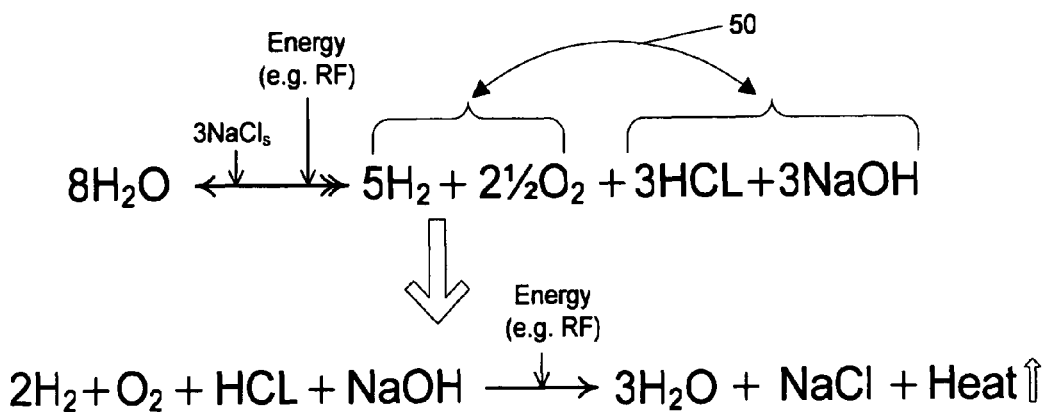
FIG. 1B is the equation and a view of the acid-base "throttle" effect.
Figure 1:
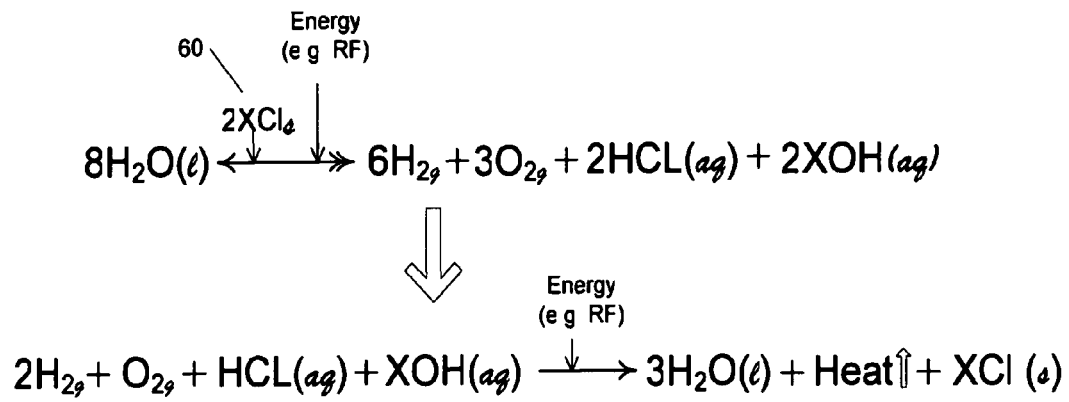
FIG. 1C is the equation and a view of the generalized form of the electrolysis and oxy-hydro combustion reaction process.
FIG. 1D is the equation and a view of the generalized form of the electrolysis and oxy-hydro combustion reaction process showing the effect of varying molar coefficients.

The equations of FIG. 1B illustrate the effect of the acid-base throttling reaction. The oxy-hydro combustion process depicted is dynamic and occurs in a fixed fluid reservoir, which necessarily results in dynamically changing concentrations of salt ions as a function of electrolytic conversion of water to elemental gas. This equation necessarily suggests that as the acid-base shift occurs in the reservoir, less and less water is available for electrolysis. This phenomenon is seen in FIG. 1B where acid-base pair 15 and 20 is shown in increased molar proportion to the normal stoichiometric quantity of base reactions 10. The reduction of available water for electrolysis is evident in the relationship 50 of oxygen and hydrogen gas to the acid-base pair. The finding is necessarily evident from the stoichiometry, namely that insufficient water is available given a fixed initial eight (8) moles of water, based on the finite reservoir of water, with increasing resulting molar concentrations of acid and base as oxygen and hydrogen are liberated from the solution in a gaseous state, such as by bubbling out of solution. As fewer moles of oxygen and hydrogen gas are present after electrolysis as in FIG. 1B, the balancing portion of atoms account for the dynamic increase acid-base concentration.

The equations of FIG. 1C demonstrate a more general case of the electrolysis and oxy-hydro combustion reaction process in which the ionic salt is represented by variable 60, where X is any appropriate group 1, period 1-7 element of the periodic table. This generalized reaction illustrates how hydronium and hydroxide ions can contribute to the same overall chemical reaction known as electrolysis and oxy-hydro combustion.

Figure 1D:
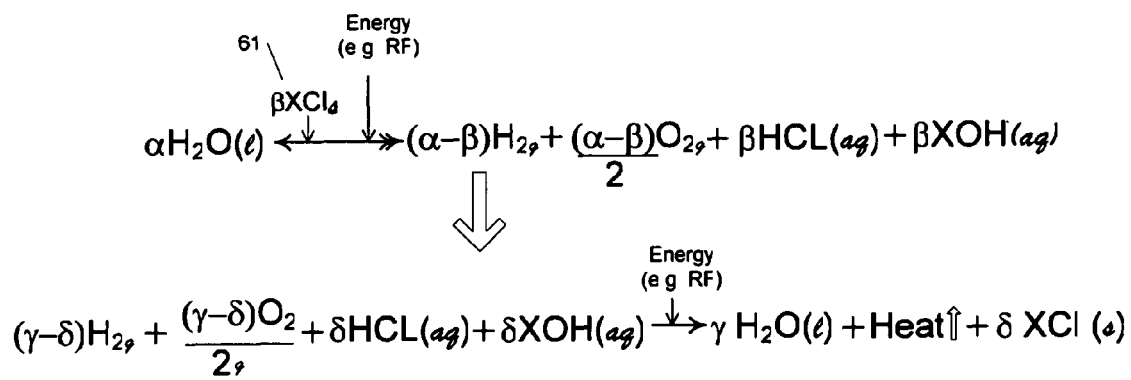

The equations of FIG. 1D demonstrate the more general case of the electrolysis and oxy-hydro combustion reaction process in which the ionic salt is represented by variables 61, consisting of $\alpha$, $\beta$, $\gamma$, and $\delta$; wherein, the molar quantities required for stoichiometric combustion are any value that appropriately satisfies the oxidation reduction valence requirements for the overall reaction. This generalized reaction case shows how oxygen and hydrogen requirements can vary and still result in the same overall chemical reaction known as electrolysis and oxy-hydro combustion.

The modes of electrolysis and oxy-hydro combustion operation described in FIG. 1A, FIG. 1B and FIG. 1C depict theoretical stoichiometric reaction processes induced by application of high frequency electromagnetic energy to a salt ion solution, including salt ion solutions typically found within biologic tissues themselves. The fundamental process is governed by the rate of electrolysis in the initial dissociation of water into oxygen and hydrogen gas, as shown in equations 10.

Based upon this understanding, methods and devices for electrosurgery can be developed that utilize one or the other, or both of the electrosurgical constituent reactions, electrolysis and oxy-hydro combustion, as further disclosed in U.S. patent application Ser. No. 10/119,671.

For example, oxy-hydro combustion can be utilized for therapeutic procedures like cutting, ablation, coagulation, vaporization, and other related procedures that are similar to those previously disclosed in the prior art. The oxy-hydro combustion reaction delivers the energy configuration necessary to cause these tissue effects and the host responses thereof as desired and described in those procedures. Electrosurgical methods and devices used for these types of procedures (see U.S. Pat. Nos. 5,669,904, 6,206,878, 6,213,999, 6,135,998, 5,683,366, 5,697,882, 6,149,620, 6,241,723, 6,264,652, 6,322,549, 6,306,134, 6,293,942, and other patents to similar effect) presumably utilize this reaction, despite the lack of recognition in such patents that electrolysis and oxy-hydro combustion is the effecter in these types of procedures (rather than plasma or related forms of ionizing radiation). In essence, in the prior art methods and devices have been developed to achieve these specific and interrelated treatment goals without fully understanding the physiochemical occurrences of electrosurgery as practiced. An inherent risk in such a situation is the possibility that iatrogenic harm and complication may occur related to the use of such methods and devices. Most notably these iatrogenic complications are due to the inability to fully contain the energy application of electrosurgery to tissue based upon the limited understanding of the physiochemical processes that are occurring. Unfortunately, since the use of such methods and devices have been increasing as electrosurgical techniques have become more popular and indications for use have been expanding, this situation is now indeed a reality, leading many practitioners and researchers to call for the guarded use of electrosurgical technology until further investigation can be completed. See, e.g., Thermometric determination of cartilage matrix temperatures during thermal chondroplasty: comparison of bipolar and monopolar radiofrequency devices. *Arthroscopy.* 2002 April; 18(4):339-46. This confusion regarding therapeutic electrosurgical protocols is typically the first clinical signal of a mismatch between science and practice, which is now leading to the reduction in use of prior art electrosurgical devices for certain applications.

The treatment methods and devices of the prior art rely upon the common denominator of tissue necrosis as the means to accomplish these treatment goals; and, this tissue effect is the main parameter employed to categorize prior art electrosurgery as a means to achieve tissue cutting, ablation, coagulation, vaporization, and the like. Most peer-reviewed studies have evaluated level of necrosis, depth of necrosis, or related parameters to quantify electrosurgical effects for these types of treatment procedures as such evaluation are most relevant in those treatment settings. Tissue necrosis occurs to some degree in all methods in the prior art due to their desired goals of tissue cutting, ablation, coagulation, vaporization, and the like. This necrosis is typified histologically by karyorrhexis or nuclear picnosis at one end of the spectrum and frank necrosis or vaporization at the other end, followed by host responses directed to the specific level of necrosis induced by the manner of tissue treatment.

Electrolysis as the initial functional reaction of electrosurgery, on the other hand, has not been explicitly recognized or exploited in the prior art for therapeutic procedures. The methods and devices developed in the prior art to achieve the treatment goals of cutting, ablation, coagulation, vaporization, and the like, have been generated without the knowledge of electrolysis as a relevant constituent part of the electrosurgical physiochemical process. This circumstance further clarifies the motivation of prior art to limit methods and devices to cutting, ablation, coagulation, vaporization, and the like that require the higher energy configurations that induce oxy-hydro combustion. Based upon this realization, methods and devices designed to provide or augment the supply of the constituents of the oxy-hydro combustion reaction have been developed and disclosed in U.S. patent application Ser. No. 10/119,671 that can bypass the relative need of electrolysis for therapeutic procedures designed to accomplish such related treatment goals as cutting, ablation, coagulation, and vaporization yet in a more expedient and efficient manner. One of the major motivations for these methods and devices, as disclosed in U.S. patent application Ser. No. 10/119,671, is to decrease tissue electrolysis for these types of treatment procedures since electrolysis induced in tissue itself is very detrimental to tissue cellular structures. It induces not only tissue necrosis quite dramatically but also transfers other significant collateral physiochemical effects that are not necessary and are additionally problematic for the treatment goals of cutting, ablation, coagulation, vaporization, and the like, as will be discussed below. These collateral effects often delay or impair healing responses of the surrounding areas of tissue treatment, expanding the depth of necrosis as described witnessed in prior art electrosurgical applications and peer-reviewed assessments. U.S. patent application Ser. No. 10/119,671 discloses further means to limit these electrolysis related detrimental tissue effects witnessed during the electrosurgical procedures of cutting, ablation, coagulation, vaporization, and the like that are realized through the understanding of the physiochemical occurrences of electrosurgery. Tissue changes and responses thereof are more fully recognized and characterized allowing additional novel uses for the oxy-hydro combustion phenomenon. In one such embodiment, tissue contact with the working electrode(s) of the instrument probe can be eliminated via the use of a translating sheath that can contain the constituents of the relevant electrosurgical reactions and place the active electrode(s) away from the tissue surface. This procedure as disclosed in U.S. patent application Ser. No. 10/119,671 benefits the tissue in that the location of electrolysis and oxy-hydro combustion occurrences is shifted from that within the tissue itself (as contemplated and practiced in prior art since the probe electrodes are used to contact the tissue to exert its effects) to that within the surrounding fluid. This shift can be partial or complete based upon the desired tissue effects of electrolysis and oxy-hydro combustion at the treatment locale. In this way, tissue electrolysis can be marginalized as a relevant occurrence in the cutting, ablation, coagulation, and vaporization treatment methods that utilize oxy-hydro combustion.

Misinterpretation of the multifaceted physiochemical occurrences of electrosurgery in the prior art has inhibited development of advancements and novel methods and devices for electrosurgical treatment beyond those that are related to cutting, ablation, coagulation, vaporization, the host responses thereof, and the like for many years.

Disclosed herein are methods and devices for electrosurgery which focus upon the electrolysis that occurs during electrosurgical procedures and exploits its occurrence as the principle means to develop methods and devices that have been heretofore unrecognized for electrosurgery. Electrolysis is a well-described phenomenon resulting from the application of electric current to an electrolyzable solution, such as a water-based solution. In a water-based solution, at the anode acid is formed by the formation of aqueous hydronium ions and the liberation of oxygen gas; at the cathode, base is formed by the formation of hydroxide ions and the liberation of hydrogen gas. When electrolysis is performed in a solution of NaCl (as would be typical of tissue in vivo), the anode produces characteristic elements. For example, chloride ions are oxidized to chlorine. Heat is also generated to a low degree, relative to the oxy-hydro combustion reaction, as heat is an artifact of inducing the electrolysis reaction. The gases of oxygen and hydrogen formed may or may not be utilized in an oxy-hydro combustion reaction depending upon whether ignition occurs.

Electrolysis has been a well recognized component in many medical applications. In such applications, treatment induces electrolysis within the tissue itself, termed "tissue electrolysis" (this term is distinct from that disclosed herein where electrolysis is not created in the tissue itself—a process hereafter referred to as "electrosurgical electrolysis" wherein the working electrode(s) do not contact the tissue to be treated and therefore do not induce tissue electrolysis). In such tissue electrolysis treatment, electric current is applied directly to tissue via various forms of electrodes for various goals such as hair removal for hirsutism, cancer cell ablation, and cardiac foci ablation to control arrhythmia. See, for example: Fosh B G et al. Electrolytic ablation of the rat pancreas: a feasibility trial. *BMC Gastroenterol* 2001 1(1):9. Since tissue in vivo is hydrated, composed primarily of water, electrolysis occurs in a typical fashion within the tissue. For example, the liberated hydrogen ions and the chlorine that one produced at the anode generally determine the extent of tissue necrosis and related findings. Electrochemical aspects of treatment of tissue with direct current. *Eur J Surg Suppl* 1994(574):111-115. Further, free radicals are formed to a lesser degree that can also induce tissue effects (Chahine R et al. Free radical generated by electrolysis reduces nitro blue tetrazolium in isolate rat heart. *Exp Toxicol Pathol* 1997 49(1-2):91-95), and the acid-base shifts that occurs (Berendson J et al. Electrochemical aspects of treatment of tissue with direct current. *Eur J Surg Suppl* 1994(574):111-115) can additionally be problematic to the tissue's ability to respond to the treatment. However, in the treatment settings where the goals are necrosis, such as hair removal, cancer cell ablation, and cardiac cell foci ablation, these effects are preferred. It is the stated intention of such methods and devices to induce necrosis to achieve the desired treatment effect.

Electrosurgery as contemplated and practiced in prior art is another manifestation of this well-described medical application of tissue electrolysis since such methods and devices operate and explicitly employ tissue contact by the working electrode(s) of the instrumentation probes to impart their treatment effects. Electrosurgery, as disclosed in the prior art, is designed to cut, ablate, coagulate, or vaporize tissues; and, in these instances, the relevance of electrolysis in any form is far overshadowed by the oxy-hydro combustion portions of the phenomenon. However, the collateral effects of surrounding tissue electrolysis are problematic for the host healing responses to such treatment, expanding depth of necrosis. In low level electrosurgical application to tissue, a method that clinically is becoming more popular (i.e. such as thermal ligament modification), the predominant effects of the treatment are those of tissue electrolysis, despite the heretofore lack of recognition as such. The histological findings of tissue treated in such a manner are typical of those induced by tissue electrolysis. Tissue electrolysis effects have been well characterized for many years. Thomsen H K et al., Early epidermal changes in heat- and electrically injured pig skin. I. A light microscopy study. *Forensic Sci Int* 1981 17(2):133-143; Thomsen H K et al. The effects of direct current, sodium hydroxide and hydrochloric acid on pig epidermis. A light microscopic and electron microscopy study. *Acta Pathol Microbiol Immunol Scand [A]* 1983 91(5):307-316. These histological findings match the histological appearance of tissue treated via prior art electrosurgery methods and devices. These effects are reviewed in U.S. patent application Ser. No. 10/119,671. Electrosurgery uses the terms tissue cutting, ablation, coagulation, vaporization, and the like, rather than tissue electrolysis to describe their tissue effect—an artifact of prior art misinterpretation of the physiochemical occurrences of electrosurgery.

For tissue electrolysis and oxy-hydro combustion, tissue effects are determined by their constituent make-up. Tissue types with high cellular content demonstrate the most relative necrosis whereas those with lower relative cellular content demonstrate a lesser propensity for necrosis in its varied forms. Tissue types like ligament which are relatively less cellular and composed of primarily extracellular matrix collagen in various cross-linking patterns typically demonstrate shrinkage due to the heat generated by the reactions, since tissue electrolysis most notably affects water-based structures. If too much heat or energy is imparted to a ligamentous structure, however, cutting, ablation, coagulation, or vaporization can occur. Electrosurgical procedures designed to shrink collagen have been well described and utilize lower energy transfer to that tissue type so that necrosis (i.e. oxy-hydrogen combustion related) does not occur to a clinically appreciable level. However, such experimentation in this area of tissue modification is conducted without the physiochemical understanding of electrosurgery. Tissue collagen sources demonstrate various shrinkage patterns and profiles as disclosed in U.S. patent application Ser. No. 09/885,749. The cells in such tissue are exposed to intracellular tissue electrolysis that creates necrosis; but, since collagen based tissue has a low requirement for resident cellular structures, relative to other tissue types, this electrolysis is often not clinically evident as necrosis to current levels of examination. Unfortunately, many instances of ligament "ablation" have been reported as a complication from prior art electrosurgical treatment as it is currently practiced. Sekiya J K et al. Autodigestion of a hamstring anterior cruciate ligament autograft following thermal shrinkage. A case report and sentinel of concern. *J Bone Joint Surg Am* 2000 October; 82-A(10): 1454-7. It has been heretofore unrecognized that the failure of collagenous structures after electrosurgical treatment is due to the effects of induced tissue electrolysis at low level energy applications. This is now easily understood to occur from cellular death induced by tissue electrolysis combined with the excessive heat production, if present, from oxy-hydro combustion. Tissue types with high cellular content or cellular structures such as cancerous cells more easily become necrotic as a result of tissue electrolysis. The electrosurgical treatment of articular cartilage has been problematic for methods and devices in the prior art. Radiofrequency energy-induced heating of bovine articular cartilage using a bipolar radiofrequency electrode. *Am J Sports Med.* 2000 September-October; 28(5):720-4. With this understanding of tissue electrolysis as a component of electrosurgery, the overlap into the arena of tissue electrolysis of the prior art is clear.

Despite the variation in tissue make-up, electrosurgery as contemplated and practiced in prior art induces necrosis at various levels of energy input for all tissue types since the clinical parameters used to determine treatment effect do not allow methods or devices to guard against such tissue necrosis (as disclosed in Patent Cooperation Treaty Application Serial No. PCT/US03/18116, entitled Methods and Devices for Electrosurgery, filed on Jun. 6, 2003). The heretofore described iatrogenic complications of prior art electrosurgery that occur at lower energy levels have been due to these direct tissue electrolysis effects, although not recognized as such prior to this disclosure. Tissue electrolysis induces tissue necrosis followed by a typical healing response to address tissue necrosis and cellular death. Oxy-hydro combustion also induces tissue necrosis, but to a much larger degree than tissue electrolysis due to the heat production and burning/vaporization of organic material that occurs. Electrosurgical procedures designed for cutting, ablation, coagulation, vaporization, and the like could utilize the tissue electrolysis reactions independently as a means to achieve such treatment goals as clearly has been the case in numerous prior art disclosures of tissue electrolysis, yet performed in endoscopic settings. In fact this realization for electrosurgery may allow a decrease in the incidence of iatrogenic damage related to unwanted tissue necrosis (depth of necrosis or collateral damage) that occurs when oxy-hydro combustion is allowed to occur during treatment.

Based upon the above disclosure, it becomes apparent to those skilled in the art that: (1) in those instances when it is desirable to induce tissue cutting, ablation, coagulation, or vaporization by electrosurgical means (i.e. high energy tissue necrosis and removal), the occurrence of electrolysis in any form is irrelevant to the procedure goals with oxy-hydro combustion serving as the relevant effecter of the procedures—essentially as disclosed in prior art electrosurgery; (2) in those instances when oxy-hydro combustion is desired and tissue electrolysis is not, such as when collateral tissue damage is to be avoided, the methods and devices of U.S. patent application Ser. No. 10/119,671 can be employed with oxy-hydro combustion as the effecter of the procedure; (3) in those instances when tissue electrolysis is desired and oxy-hydro combustion is not, i.e. a lower energy transfer to tissue, the methods and devices of many prior art tissue electrolysis disclosures can be utilized; and (4) in those instances when the effects of electrosurgical electrolysis are desired without tissue electrolysis or oxy-hydro combustion, the methods and devices disclosed herein can be utilized. Further, it is intended that the disclosures of Patent Cooperation Treaty Application Serial No. PCT/US03/18116, entitled Methods and Devices for Electrosurgery, filed on Jun. 6, 2003, allowing the sensing, measuring, and detection of the relevant parameters of electrosurgery, provide an added means by which these reactions can be separated during in vivo application to guard against undesired physiochemical occurrences in any given specific treatment protocol.

The previous discussion indicates that the electrosurgical process in its current form, although previously unrecognized as caused by tissue electrolysis and oxy-hydro combustion, has been design-limited to induce various levels of tissue necrosis in the form of cutting, ablation, coagulation, vaporization, and the host responses thereof. This understanding places prior art electrosurgery methods and devices into the category of inducing various levels of tissue necrosis by way of tissue electrolysis and/or oxy-hydro combustion. Since tissue electrolysis has been long studied and utilized in many forms, methods and devices designed to induce tissue electrolysis via electrosurgery are simply another way of inducing tissue necrosis or vaporization. Next generation methods and devices as disclosed in U.S. patent application Ser. No. 10/119,671 can be used to decrease the relevance of tissue electrolysis and its associated detrimental collateral physiochemical effects discussed above for those procedures.

Disclosed herein are methods and devices designed to utilize the electrolysis portion of the electrosurgical process in novel and heretofore unrecognized ways that do not rely upon tissue electrolysis, tissue necrosis, or oxy-hydro combustion. Therefore, the methods and devices disclosed are not intended for cutting, ablation, coagulation, vaporization, and the like. Disclosed also are means to contain the electrosurgical physiochemical occurrences to decrease detrimental effects and collateral tissue damage as seen in prior art. Disclosed is the utilization of the electrolysis portion of the electrosurgical reactions to induce antimicrobial effects and host healing responses for various treatment procedures and goals unrelated to cutting, ablation, coagulation, vaporization, and the like. Since, however, as discussed above, tissue electrolysis induces tissue changes that induce necrosis and other problematic physiochemical collateral tissue effects that would not be helpful for methods and devices designed to induce antimicrobial and host healing responses, other methods and devices are necessary to achieve these treatment goals. The methods and devices disclosed herein center around utilizing interfacing media and/or materials that are applied to tissue in vivo before, after, or concurrently with the application of electromagnetic energy such as radio frequency energy to the interfacing media and/or materials to induce electrolysis within the interfacing media and/or materials, thus activating the interfacing media or material. The electrolysis induced within the interfacing media and/or materials consequently induces characteristic products of the electrolysis reaction at both the anode and the cathode. Other characteristic products can be formed based upon the other elements that attend the electrolysis reaction (i.e. NaCl). These products are now utilized in electrosurgical procedures to novel ends to achieve the interrelated treatment benefits of (1) antimicrobial effects, (2) enhancement of host healing responses, (3) local non-detrimental heat generation, and (4) oxygenation of treated tissue. It now becomes clear to those skilled in the art that any interfacing media or material that retains a water base capable of electrolysis via the application of electromagnetic energy, and particularly radio frequency energy, can be used to create media or materials that can serve as the effecter of the electrosurgical electrolysis process that is translated to tissue either in vitro or in vivo. Further, the interfacing media or material is preferably acellular to avoid sequelae of "tissue electrolysis"; and, therefore no untoward effects of electrosurgical electrolysis occur within the interfacing media or material which may be problematic for cellular viability. However, a layered, composite, or hybrid interfacing material (the treatment composite) is one such embodiment in which the activation component consists of an acellular water-based substance that can be activated by electromagnetic energy application to induce electrolysis, which effects are then transferred to the other components which themselves may retain cellular structures required for certain treatment applications. Further, it is anticipated that the interfacing media or material may be impregnated with such other elements that may be deemed important for the particular treatment protocol and which may be activated or delivered to the treatment site by the methods and devices disclosed herein. Further, it is anticipated that the interfacing media or material will be activated either within treatment devices themselves or within other biocompatible chambers designed for specific treatment protocols. These chambers may themselves be therapeutic and part of the treatment composite, complementing the methods and devices disclosed herein. Further, instrumentation devices are disclosed that focus upon the efficient induction of electrosurgical electrolysis relative to the specific interfacing media or materials that also do not allow either tissue electrolysis or the ignition of the products of electrolysis to oxy-hydro combustion that would not be desired in such treatment applications. It is further contemplated that such devices as disclosed herein are to be used with those methods and devices as disclosed in Patent Cooperation Treaty Application Serial No. PCT/US03/18116, entitled Methods and Devices for Electrosurgery, filed on Jun. 6, 2003, whereby these goals can be more accurately assured. In these applications, the working electrode(s) of the electrosurgical device does not contact the tissue to be treated, representing a new and novel treatment approach for electrosurgery methods and devices.

The following calculations illustrate that a "plasma" does not contribute significantly to the overall clinical effect of electrosurgery. The energy current needed to vaporize water and then sufficiently ionize the remaining molecules into a plasma is beyond the energy input of the electrosurgical system. Further, the electrosurgical system exhibits impedance rather than conductivity within the effecter area.

The phenomenon of electrolysis and oxy-hydro combustion provides a more accurate alternative to the plasma paradigm. It is generally accepted that an electrosurgical probe system must create a "vapor pocket" immediately about the active electrode surface in order for any plasma-like activity to become evident. As an example, this requires the complete vaporization of a 0.9% by weight solution of sodium-chloride in deionized water. Any such dilute solution will result in a boiling point elevation and require additional energy input to reach the saturated vapor state. The typical boiling point elevations for such solutions range from 1%-5% and can be considered negligible for the purposes of this exercise (i.e. a saline solution will not boil at exactly 100° C., but rather on the order of 101° C. to 102° C. depending on the specific ambient pressure conditions of the fluid field). If we assume that water makes up the bulk of the components in question and look to the thermodynamic requirements to boil water on a per-pound-mass basis, it is known that:

$$m \cdot Cp_{H_2O} \cdot \Delta T = 1150.4 \frac{BTU}{Lb_m} = Q_{LHV}$$

When converted to Watts on a per second basis:

$$Q_{LHV} = 1213.7 \frac{kW}{Lb_m}$$

If we consider that the amount of fluid immediately surrounding the electrode tip is on the order of one-hundredth of a fluid ounce (0.01 oz.), then the energy of vaporization converted to a per-second basis is:

$$Q_{LHV} = 790 \frac{W}{(0.01)Oz.}$$

From this simple thermodynamic analysis, it is evident that given generic electrosurgical console output on the order of 180-260 W/sec, a large portion of the energy present is required to initiate vaporization at standard temperature and pressure (STP) conditions. This approximates 3 seconds of full power input to create an adequate vapor pocket for any "plasma" to begin forming. Furthermore, additional energy input beyond the latent heat of vaporization (LHV) is required to perform additional molecular excitations that would result in the stripping of electrons from the constituent atoms within the gaseous solution. It appears that a disproportionate amount of energy would be required to maintain the basic continual vaporization of water as it is continually refreshed in the surgical environment, i.e. not in a fixed pressure vessel, let alone perform higher energy dissociations of constituent sodium atoms.

In an alternative analysis, it is noted that plasma states of matter, as highly ionized gas conditions, are known to be excellent electrical and thermal conductors due to the rapid Brownian motion of the constituent atomic particles and freely available electrons for conduction of current. This suggests some specific behavioral characteristics which can be illustrated simply.

Given that the ionization energies of typical atomic elements can be expressed as:

$$X \rightarrow X^+ + e^-$$

and given that this value is known for sodium (D. W. Oxtoby, N. H. Nachtrieb. *Principles of Modern Chemistry*. Saunders College Publishing, N.Y., N.Y. 1986; pp. 438-439):

$$IE_1 = 496 \text{ kJ/mol}; IE_2 = 4562 \text{ kJ/mol}$$

and given that these values can be converted to Watts:

$$495,720 \frac{W \cdot Sec}{Mol}$$

Then given a 0.01 oz. estimate of the total volume of the saline fluid immediately surrounding the active electrode approximating the basic density of the fluid to be equivalent to that of water (a reasonable approximation), the mass of fluid can be calculated:

$$1.0443 \times 10^{-5} \text{ ft}^3 \cdot 62.4 \frac{Lb_m}{ft^3} = 6.48 \times 10^{-4} Lb_m$$

At the standard solution content of 0.9% by weight NaCl:

$$6.48 \times 10^{-4} Lb_m \times 0.009 = 5.8 \times 10^{-6} Lb_m(\text{NaCl})$$

Converting value to grams yields:

$$2.6 \times 10^{-3} \text{ gr(NaCl)}$$

Given the molecular weight of NaCl, 58.44 gr/mol, it is clear that only a fraction of a mole of the sodium chloride is present:

$$4.44 \times 10^{-5} = Y_{fraction}$$

By corollary, a similar order of magnitude fraction exists for sodium alone. Thus, it can be estimated that a $10^{-5}$ molar proportion of sodium is present at the electrode tip and would require additional ionization energy $IE_1$ on a per-second basis as follows:

$$496 \frac{kJ}{Mol} \cdot 1 \times 10^{-5} Mol(Na) = 4.95 \cdot Watts$$

This energy is in addition to that required to maintain continual vaporization of the saline fluid. Thus, the total minimum energy required to maintain any plasma-like activity immediately about the electrode tip can be described as the sum of $IE_1$ and LHV. Mathematically, on a per-second 0.01 oz. basis:

$$IE_1 + Q_{LHV} = 4.95 \cdot W + 790 \cdot W \approx 795 \cdot W$$

This result remains in discord with the fact that most common electrosurgical consoles are only capable of emitting 250 Watts of electrical energy. More than triple such energy is required to satisfy the thermodynamics of plasma creation.

The electrical conduction characteristics of all plasmas are fairly well known and are most plainly called conductors. Plasmas do not exhibit high impedance characteristics that are common to simple gas volumes. Because they are highly ionized, there are sufficient free electrons to easily conduct current and as such do not provide significant impedance to current flow. The response curve of a typical electrosurgical probe from a power versus impedance standpoint is significantly different from typical plasma behavior. In the fluid state prior to "vapor pocket" formation, electrical conduction dominates the mode of transmission and impedance slowly rises with the temperature of the fluid. When vaporization results in nucleate boiling, the impedance begins a sharp rise and immediately "spikes" when full film boiling is initiated, i.e. the "vapor pocket." A generic characteristic curve for a plasma's impedance profile once established, and a characteristic curve for the impedance versus power of a typical immersed electrosurgical probe, are included in Patent Cooperation Treaty Application Serial No. PCT/US03118116, entitled Methods and Devices for Electrosurgery, filed on Jun. 6, 2003.

It is evident that plasma would not behave electrically as does operation of an electrosurgical probe, because plasma would be an ideal conductor and show net reduced impedance to current flow once plasma was established. This is clearly not the case in the manifestation of a typical electrosurgical probe.

For the purposes of further analysis, the thermo-chemical approximations of water rather than a 0.9% NaCl aqueous solution can be utilized, again underestimating energy requirements, on the assumption that the initial state of the water starts out at approximately 25° C. and must result in full film boiling, approximately 100° C., to sustain the "vapor pocket" required for a "plasma." If the volume of water that is to be affected equals 0.3 cm³, then to initiate full film boiling:

$$Q_{SV} := \frac{Cp_{H20}}{MW_{H20}} \cdot (75K) \cdot 0.3 \text{ g}$$

Such that:

$$Q_{SV} = 94.073 \, J$$

This is the energy input required to achieve the saturated liquid state. Insufficient energy exists to fully vaporize water; for that an additional energy input is required, the energy of vaporization or LHV. Therefore, further input of the following amount of energy is required (Lide D R, Ed. *CRC Handbook of Chemistry and Physics*. CRC Press, 83rd edition, 2002):

$$Q_{LHV} := 1150.4 \frac{Btu}{lb} \cdot 1055.5 \frac{J}{Btu} \cdot 1 \frac{lb}{453.6 \text{ g}} \cdot MW_{H_2O}$$

Such that:

$$Q_{LHV} = 4.821 \times 10^4 \frac{J}{mol}$$

Thus, the total energy required to maintain a saturated "vapor pocket" would require a total energy input of:

$$Q_{input} := Q_{SV} + Q_{LHV} \cdot 0.3 \frac{g}{MWH_2O}$$

Such that:

$$Q_{input} = 897.146 \, J$$

If it is assumed that it is actually plasma that is the driving force that will generate the 897.14 J required to vaporize the water, it is easy to evaluate the "plasma current" that is required to achieve this profile. The energy input would be required to produce EV particles in at least the quantity of the LHV and actually requires additional energy beyond this as the water is consuming it in a change of state process. Thus, using the LHV as a benchmark for the energy input, as it is the absolute minimum requirement for a plasma, it then follows that the actual number of elementary charged particles required to vaporize the 0.3 g sample of water is:

$$\frac{Q_{input}}{eV} = 5.6 \times 10^{21} \text{ particle}$$

using the average energy/particle=1 KeV, which is based upon the average electric field to which all the particles would be subject. This value is equivalent to the field produced by a typical electrosurgical generator at full power where Vpk-pk~1 kV or 1 keV. To properly account for the aggregate charge of the particles, the total number of particles is divided by 1,000, thus yielding:

$$\frac{Q_{input}}{eV \cdot 1000} = 5.6 \times 10^{18} \text{ particle}$$

1 keV particles at the ambient electric field strength produced by a typical electrosurgical generator, which is a fraction of a coulomb as follows:

$$\frac{Q_{input}}{eV \cdot 1000 \cdot ParticlesperCoulomb} = 0.897 \, C$$

or:

$$\frac{Q_{input}}{eV \cdot 1000 \cdot ParticlesperCoulomb} = 0.897 \text{ sA}$$

This value can be classified on a per second basis as 0.9 Amp of "Arc-Current" (an extremely high current flow for an arc). It is clear that with approximately 90% of a Coulomb of charged particles there is ample availability for conducting electricity. In fact, at such a high concentration of charged particles the net resistance of any such volume would be extremely low. This finding conflicts with the behavior of the typical electrosurgical probe which exhibits a "capacitor" like behavior at the point of "plasma-like" transition. Such behavior should not be present with nearly a Coulomb of particles to conduct current. The net resistance of the system should drop at the point of plasma formation to near zero.

Antimicrobial effects are induced by this process. Electrolyzed strong acid water (also referred to as acidic oxidative potential water, function water, or acqua oxidation water) has been recently developed in Japan. It is a strong acid formed on the anode in the electrolysis of water containing small amounts of NaCl. Its properties generally include a pH between 2.3 and 2.7, an oxidative-reduction potential between 1,000 and 1,100 mV, dissolved chlorine between 30 and 40 ppm, and dissolved oxygen between 10 and 30 ppm. These properties exert strong antimicrobial effects.

For example, the bactericidal activity of electrolyzed strong acid water containing free chlorine has been recently reviewed. Kiura H et al., Bactericidal activity of electrolyzed acid water from solution containing sodium chloride at low concentration, in comparison with that at high concentration. *J Microbiol Methods* May 49(3):285-293, 2002. The use of such electrolyzed strong acid water has been limited to that of a disinfectant for the treatment of medical instruments as its properties are too corrosive for tissue application. Newer configurations have been developed that utilize a less strong acid component for similar applications that are less damaging to medical instruments themselves. The bactericidal mechanism of action has been described as including disruption of the bacterium's outer membrane and inactivation of cytoplasmic enzymes.

Electrolyzed acid water has also been demonstrated to exert disinfection potential against virus such as hepatitis B and human immunodeficiency virus. Morita et a. Disinfection potential of electrolyzed solutions containing sodium chloride at low concentrations. *J Virol Methods* 2000 March 85(1-2):163-174. Electrolysis of 0.05% NaCl in tap water for 45 minutes at room temperature by a 3 A current generated an oxidation-reduction potential of 1053 mV, a pH of 2.34, and a free chlorine content of 4.20 ppm that was effective in modifying antigenicity and infectivity in both a time and concentration dependant manner. Electrolyzed acid water has been used as a disinfectant for other such pathogens such HCV, CMV, and fungi in a similar fashion.

The transition to the use of electrolyzed acid water in vivo upon tissue has been difficult due to the agent's corrosive properties, namely those which induce microbicidal activity. Therefore, other configurations have been developed. For example, lavage of infected tissues several times a day for multiple days has been successful in some instances. Inoue et al. Trial of electrolyzed strong acid aqueous solution lavage in the treatment of peritonitis and intraperitoneal abscess. *Artif Organs* 1997 January 21(1):28-31; Sekiya S et al. Treatment of infectious skin defects or ulcers with electrolyzed strong acid aqueous solution. *Artif Organs* 1997 January 21(1):3-38. Direct irrigation of the porcine pancreas for xenotransplantation has prevented bacterial contamination of the organ; however, direct irrigation of pancreatic islet cells themselves decreases cellular viability and function. Miyamoto et al. Effectiveness of acidic oxidative potential water in preventing bacterial infection in islet transplantations. *Cell Transplant* 1999 July-August 8(4):404-411. These reports indicate difficulty in applying electrolyzed acid water to tissue in vivo for the purposes of its antimicrobial effects when cell viability is important.

The induction of interfacing media or material electrolysis via the methods and devices disclosed herein allow the use of these antimicrobial properties.

Enhancements of host healing responses are induced by this process. Electrolyzed water accelerates the healing of full-thickness cutaneous wounds. Yahagi et al. Effect of electrolyzed water on wound healing. *Artif Organs* 2000 Dec. 24,12:984-987. Such healing augmenting properties have been determined to not be due to the antimicrobial properties of the electrolyzed water, but rather to be due to induction of cell migration and proliferation, like fibroblasts, by the reactive oxygen species present in the solution. Operative sites and other wounds typically heal by a defined series of mechanisms, orchestrated by cells at a number of levels. The function of such cells is ubiquitous in living organisms; and, such cells include types such as connective tissue stem cells, phagocytic cells (histiocytes), protein secreting cells (fibrocytes), and contractile cells (myofibroblasts). These cells are responsible for healing responses and homeostasis in all tissue types like bone, cartilage, ligament, tendon, connective tissue, and the like. The stimulation or chemotaxis of cells to produce products of transcription that participate in the healing response is their predominant orchestrating. Collagens (i.e. types I, III, V, VI, IX), fibronectins, glycoproteins, glycosaminoglycans, proteoglycans, collagenases, proteoglycanases, plasminogen activators, interleukin-1, interlukin-6, granulocyte colony-stimulating factors, granulocyte macrophage-colony stimulating factors, transforming alpha and beta growth factors, and tissue inhibitor of metalloprotinases are just some of the products that assist in the healing response orchestrated by these cells. Further, these cells can regulate immunoglobulin synthesis, B cell growth, and bone marrow release of leukocytes. Stimulants to such cell function and migration to an injury or treatment site include mechanical loading like stretch and pressure and from immunologic influences such as platelet derived growth factors, lymphocyte derived chemotactic factor for fibroblasts, hydroxyproline containing peptides, tropoelastin peptides, TGF-$\beta$, and leukotriene B$_4$, acid and basic fibroblast growth factors, reactive oxygen species as induced by electrosurgical electrolysis, and the like. It is via the effects of electrolysis, namely low level oxygen free radical production, that such cellular induction occurs initiating this cascade. Further, tumor necrosis factor production and the activity of natural killer cells increase in a similar fashion. Fesenko E E et al. Immunomodulating properties of bidistilled modified water. *Biofizika* 2001 March-April 46(2):353-358].

The induction of interfacing media or material electrolysis via the methods and devices disclosed herein allow the use of these cell stimulating properties.

Local non-detrimental heat production is induced by this process. Aqueous media or materials when subjected to electrolysis generate a low level of heat. This heat is produced both convectively and conductively during the process with the electrosurgical methods and devices disclosed herein. Normal tissue healing responses are attendant by a slight increase in local temperature. This increase of temperature mobilizes the healing response at many levels such as the host inflammatory response, changing sensitivity of local enzymatic processes, availability of elements such as zinc aiding leukocyte function, inducing increased blood flow and perfusion, and transcription induction of the heat stimulated DNA sequences. Further, the contractile nature of wound healing is related to increased heat at the healing site, aiding the non-contractile elements (as opposed to those based upon active elements like myosin or actin) such as collagen fibrils to contract or shrink. Such heat also suppresses bacterial multiplication, allowing phagocytic cells greater opportunity to remove the microbes. By slightly increasing the locale temperature by the energy attendant to the electrolysis process as disclosed herein, the benefits of systemic fever are mimicked locally. These findings provide a rationale for additional methods and devices that utilize the electrolysis reaction as the effecter in treatment protocols.

The induction of interfacing media or material electrolysis via the methods and devices disclosed herein allow the use of this low level heat production.

Oxygenation of the treated tissue is induced by this process. Hyperbaric oxygen treatment is a well known method of aiding tissue healing. Hyperbaric oxygen functions via the elevation of the oxygen partial pressure at a tissue site. See, for example, Senior C. Treatment of diabetic foot ulcers with hyperbaric oxygen. *J Wound Care* 2000 April 9(4):193-197. One mechanism of this function is via cell stimulation. For example, fibroblasts synthesize and modify collagen as part of the wound healing cascade. For such cellular activity, high partial pressures of oxygen are required above that which is normally present in the homeostatic state (when healing responses are not required). The elevation of oxygen partial pressure around a cell induces such cellular activity. Another mechanism by which increasing partial pressure of oxygen can aid tissue healing is by vasodilatation and vascular proliferation. Increasing oxygen partial pressures at the healing treatment site also exerts an antimicrobial effect upon anaerobic organisms.

The induction of interfacing media or material electrolysis via the methods and devices disclosed herein allow the use of increased local oxygen partial pressure.

The devices and methods disclosed herein are designed (1) to decrease the incidence of operative site and/or wound infection by providing antimicrobial activity and/or augmenting treatment of infected operative sites when necessary, (2) to induce healing responses or therapeutic at the treatment site orchestrated by the stimulation of resident cellular function, (3) to induce healing responses or therapeutic benefits at the treatment site via local non-detrimental heat production, and/or (4) to induce healing responses or therapeutic benefits at the treatment site via oxygenation of the treated tissue and site. Other beneficial effects of the electrolysis reaction will become evident to those skilled in the art when applied via the methods or devices disclosed herein. The methods and devices utilize electromagnetic energy, and preferably radio frequency energy, to induce electrolysis of a water-based media or material that is applied to a treatment site either in vitro or in vivo. Such methods and devices allow utilization of electrosurgical procedures that induce antimicrobial and host healing responses as well as therapeutic benefits by creation of interfacing media and materials which are activated by electromagnetic energy, and preferably radio frequency energy, inducing electrosurgical electrolysis and which thereafter translate these effects to the tissue to which they are in contact. In this manner, the working electrode(s) of the electrosurgical devices themselves does not directly contact the tissue to be treated, a distinction from the prior art, eliminating the induction of tissue electrolysis that causes necrosis and has been problematic for prior art electrosurgical procedures in treatments other than cutting, ablation, coagulation, vaporization, and the like. The interfacing media or material becomes a treatment vehicle which is activated by the application of electromagnetic energy such as radio frequency energy. Further, the interfacing media or material can be impregnated with any other material that is deemed appropriate for the particular treatment goals that itself can be activated via electrosurgical energy transfer. Further, the treatment chamber that contains the electrosurgical electrolysis itself can be configured in such a manner to augment therapeutic protocols. For instance, it is anticipated that the interfacing media or material will be activated either within treatment devices themselves or within other biocompatible chambers designed for specific treatment protocols and that these chambers may themselves be therapeutic and part of an electrosurgical tissue treatment composite.

Figure 2:
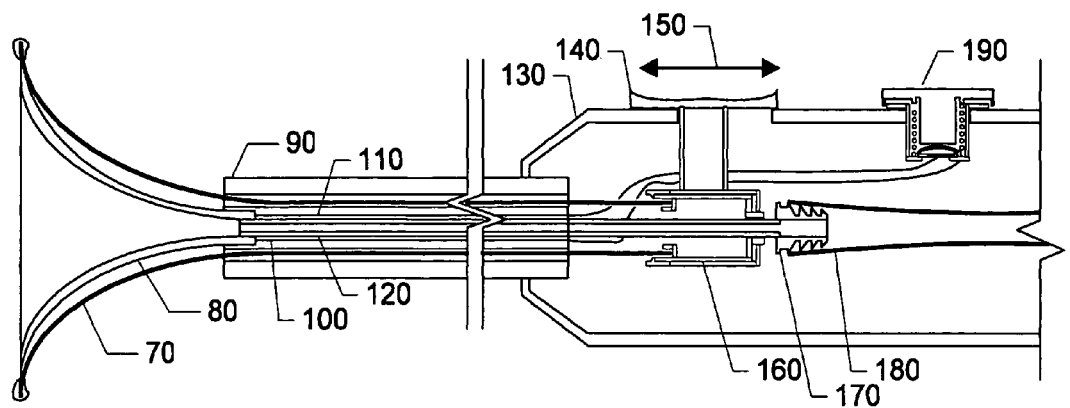
FIG. 2A is a view of a non-contact electrosurgical probe apparatus of the invention with a retractable transparent elastomeric trumpet electrosurgical chamber.
FIG. 2B is a view of the transparent elastomeric trumpet electrosurgical chamber of FIG. 2A in the fully extended condition with the active and return electrode traces visible.
Figure 2:
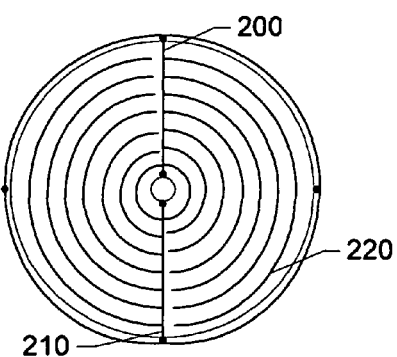

FIG. 2A illustrates a non-tissue contacting electrode electrosurgical probe apparatus wherein the use of flexible printed electrode trumpet cup 80 on which is disposed electrode traces 200, 210, and 220 that conduct electromagnetic energy. The trumpet cup is retractable via means provided in handpiece 130 wherein is disposed movable switch 140 that is translatable in proximal and distal directions as shown by arrow 150. When movable switch 140 is translated, the force of motion is transmitted to actuator/lumen coupler 160 which translates forward force to shape memory extension push-wires 70. Simultaneously coupled at actuator lumen/coupler 160 is flexible injection lumen 120 which translates in tandem with flexible transparent polymer trumpet cup electrode 80. When acting in concert, the combination of elements 70, 160, 80, 200, 210, and 220 form a non-tissue contact electrode chamber when applied with minimal force to a tissue structure. Electrosurgical electrolysis, and optionally oxy-hydro combustion, is initiated by activating switch 190. Additional fluids of various types can be injected into the interface chamber via flexible injection tubing 180 and injection adapter 170. As will become apparent to those skilled in the art, the ability to monitor the relevant parameters of electrosurgery as described in Patent Cooperation Treaty Application Serial No. PCT/US03/18116, entitled Methods and Devices for Electrosurgery, filed on Jun. 6, 2003, may be utilized to monitor and control the process that occurs within this chamber.

FIG. 2B illustrates the interior of transparent polymer trumpet cup electrode 80 wherein disposed is diverging active electrode trace pattern 220 that conducts electromagnetic energy in opposing semi-circular manner to provide total chamber electrification away from the tissue to be treated, thereby avoiding tissue electrolysis. Electromagnetic energy is supplied via an electrosurgical generator and conducted to switch 190 which closes upon activation to energize active and return conductors 100 and 110. The conductors in turn run the length of malleable support lumen 90 and supply traces 200 and 210 with electromagnetic energy that provides means for the opposing semi-circular electrode patterns 220 to provide trumpet space electrification. The use of the electrified trumpet chamber provides a controllable means by which its content can be altered to treat tissue or to provide further means for infiltrating or bathing tissue and cells with therapeutic components via flexible injection tubing 180 adjacent to such treated tissue.

Figure 3:
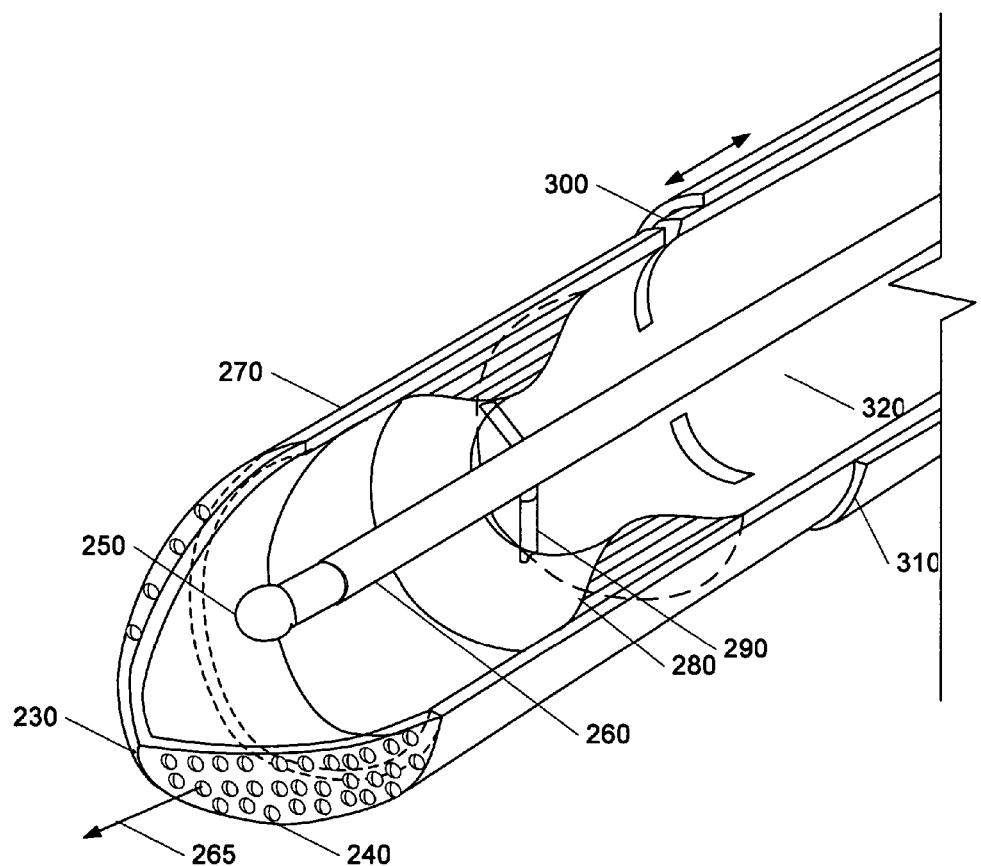
FIG. 3 is a view of a non-contact electrosurgical electrolysis probe apparatus of the invention with a different electrosurgical chamber configuration.

FIG. 3 illustrates a non-tissue contacting washing electrosurgical probe apparatus wherein disposed is a thermal gradient flow delivery system. Intermediary fluid enters the probe via inlet portals 300 which can be regulated by altering the cross-sectional area available for fluid ingress via translating inlet portal flow regulator 310. In the static state just prior to activation the entire internal volume of the probe exists in the wetted condition. As electromagnetic energy is delivered to active electrode 250, ordinary propagation heating effects alter the temperature of the fluid immediately proximal to perforated active electrode shield 230. As the temperature of the active electrode 250 continues to rise with increasing energy input so does the surrounding fluid. Because the fluid external to the perforated active electrode shield 230 exists at the free stream temperature (i.e. 50° F. to 70° F.), a convective thermal gradient is established. The thermal gradient drives the hotter fluid inside the active electrode/perforated active electrode shield chamber through individual perforations 240, thereby accelerating and helping to laminar the flow. Active electrode 250 is externally insulated by an external insulator sheath 260 which prevents the flow of current between active electrode 250 and return electrode 270 in tandem with internal insulation sheath 320 which runs the entire internal length of lumen. Active electrode 250 is stabilized by active electrode vane supports 290 to prevent electrolysis convection or oxy-hydro combustion cavitation forces from bending the electrode 250 into contact with internal wall sections. Fluid transport is further enhanced by accelerating venturi section 280 that induces a velocity/momentum increase to the fluid as part of the conservation of mass flow. The driving force behind this is the thermal gradient created by active electrode 250 firing and flowing fluid out through perforated active electrode shield chamber 230. What will become apparent to those skilled in the art is the ability to provide localized non-tissue-contacting electrosurgical washing of tissue structures without the need to couple a lumen section to a pressurized fluid feed system. By utilizing naturally occurring thermal gradients and convective flow forces, a directed fluid flow is created that can be imparted upon tissue structures within the human body to reap the therapeutic benefits of said flow components. As will become apparent to those skilled in the art, the ability to monitor the relevant parameters of electrosurgery as described in Patent Cooperation Treaty Application Serial No. PCT/US03/18116, entitled Methods and Devices for Electrosurgery, filed on Jun. 6, 2003, may be utilized to monitor and control this process.

FIG. 2A, FIG. 2B, and FIG. 3 describe instrumentation embodiments that can be used with various interfacing media or materials by way of creating a chamber for the electrosurgical electrolysis process whereby the working electrode(s) does not contact the tissue to be treated but the interfacing media or material does. Most notably, configurations of various interfacing media and materials such as liquids like endoscopy or tissue irrigants or other configurations like hydrogels, waxes, biopolymers, and the like can be applied, wherein such interfacing materials are placed within the chamber or body of the devices discussed above and then deployed via the effects of the electrosurgical methods disclosed herein. Further, Patent Cooperation Treaty Application Serial No. PCT/US03/18116, entitled Methods and Devices for Electrosurgery, filed on Jun. 6, 2003, provides further methods and examples of such elements, and is incorporated herein.

As a further clarification of the scope of the electrosurgical application of this disclosure, FIG. 4, FIG. 5A, FIG. 5B, FIG. 10, and FIG. 11 illustrate methods and devices as applied to tissue wound sites. In these examples, the interfacing media or materials themselves do not require significant structural rigidity or mechanical strength in order to be effective for treatment goals and can be applied in a less defined or less rigid chamber setting.

Figure 4:
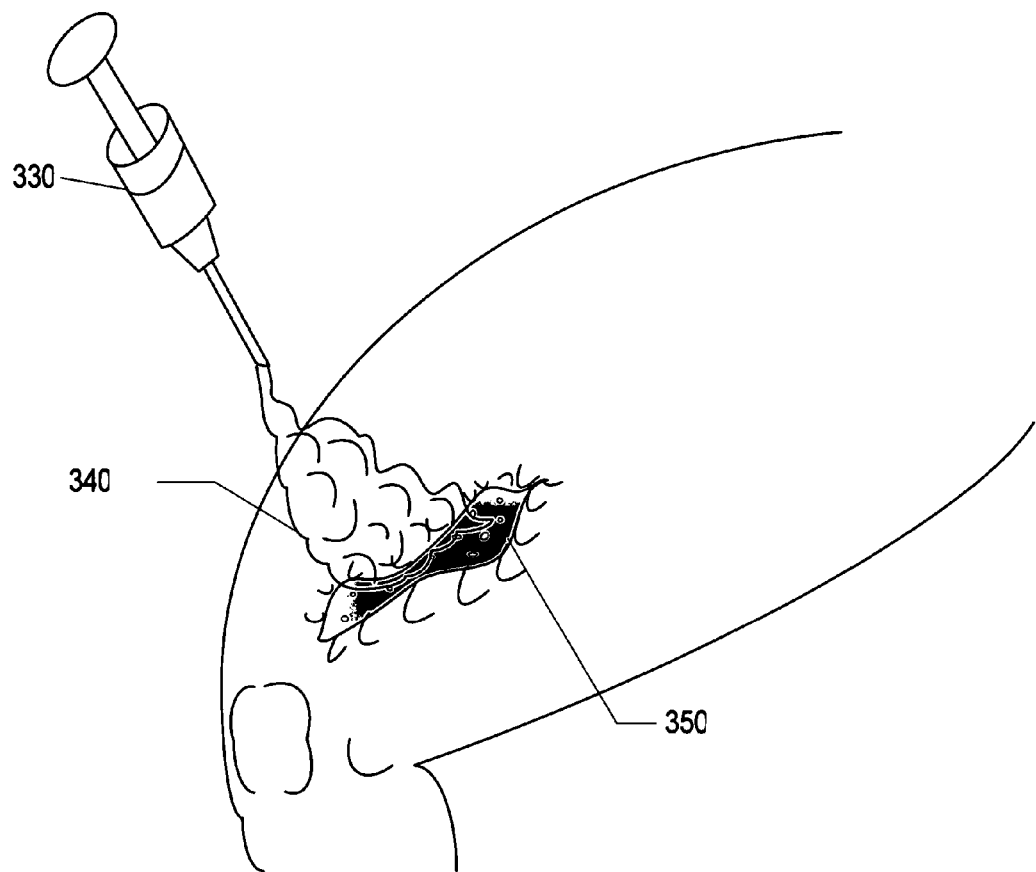
FIG. 4 is a view of the application of an electrosurgical electrolysis interfacing material of the invention to a wound site.

FIG. 4 illustrates the use of a hydrogel 340 as an interfacing material within a wound site 350. Hydrogel 340 is comprised of hydrophilic polymer that is water soluble in a large range of temperatures and pH. Some such polymers are derived from natural sources known in the art such as agar, gelatin, carboxymethylcellulose, hyaluronan, alginic acid, and many others. Upon injection from syringe 330 into the wound site 350 the hydrogel may be activated with an electrosurgical probe configuration as disclosed herein to perform electrolysis of the hydrogel as an interfacing media or material.

Figure 5A:
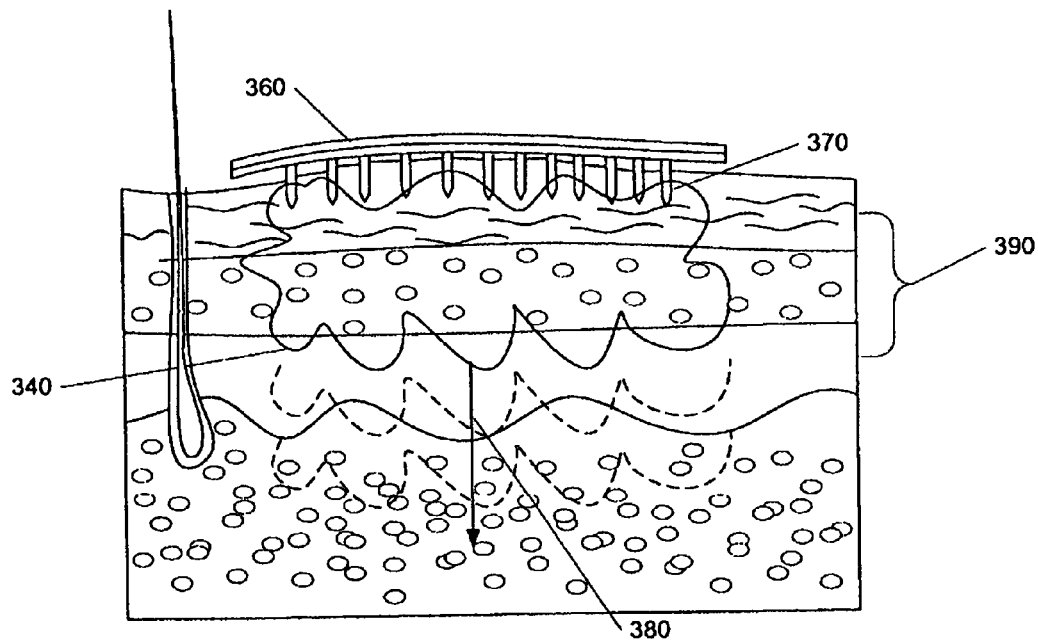
FIG. 5A is a view of a direct current photo-voltaic wound treatment system of the invention.
Figure 5:
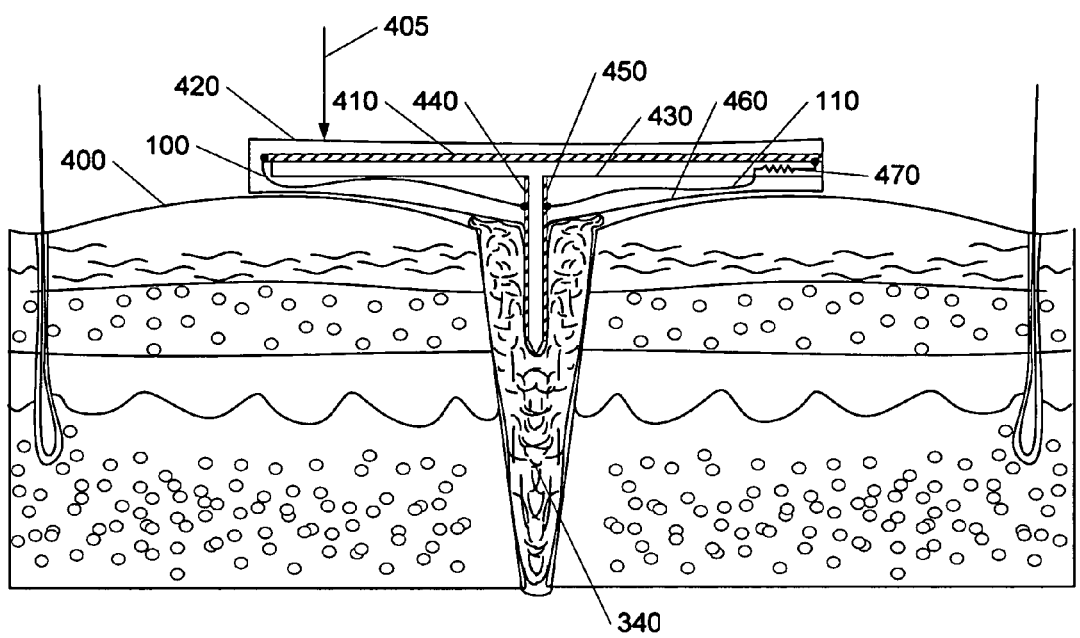
FIG. 5B is a view of a direct current photo-voltaic wound treatment system of the invention interacting with an electrosurgical electrolysis interfacing material.

FIG. 5A and FIG. 5B illustrates the use of a photo-voltaic wound treatment device 360. Independent tines 370 form a part of active and return electrodes that penetrate the wound site subcutaneously and make physical contact with interfacing media or material 340, thereby inducing a current flow through the interfacing media or material and inducing electrolysis therein. As the electrolysis process progresses within interfacing media or material 340, its viscosity alters both from chemical makeup alterations as well as localized heating induced by electrolysis, contributing to net interfacing media or material propagation 380 deeper into the wound site. The localized electrolysis of the hydrogel as an interfacing media or material induces the benefits disclosed herein. Photonic energy 405 impacts transparent protective coating 420 and traverses to photo-voltaic thin film generator 410. The photonic energy thereby induces a voltage in aggregate that is conducted via active electrode wire 100 to direct current active electrodes 440 that may include a single active electrode film such as a foil or film of silver that behaves like an array of independent electrodes. Current is conducted through interfacing media or material 340 to current return electrode 450 via return electrode conductor 110 to load balancing resistor 470 to close the current loop at the negative side of photovoltaic generator 410. Active and return electrodes are separated by support member 430 comprised from the many varieties of insulating polymers that are biocompatible. The entirety of the photo-voltaic wound treatment device may be held in place by epidermal adhesive coating 460 that adhesively bonds the device to epidermis 400 while simultaneously providing wound closure means that is hypoallergenic, such as is familiar to those skilled in the art of surgical tape manufacture. Electrode tines 370 are easily manufactured from bioabsorbable substrates coated with thin-films of gelatinized sodium chloride to provide means for a biocompatible, bioabsorbable active and return electrodes. Additionally such bioabsorbable tines can also be manufactured as frangible elements to allow the easy removal of the photo-voltaic adhesive portion by the patient themselves, similar to that of current band-aid technology commercially available over the counter to consumers.

Figure 10:
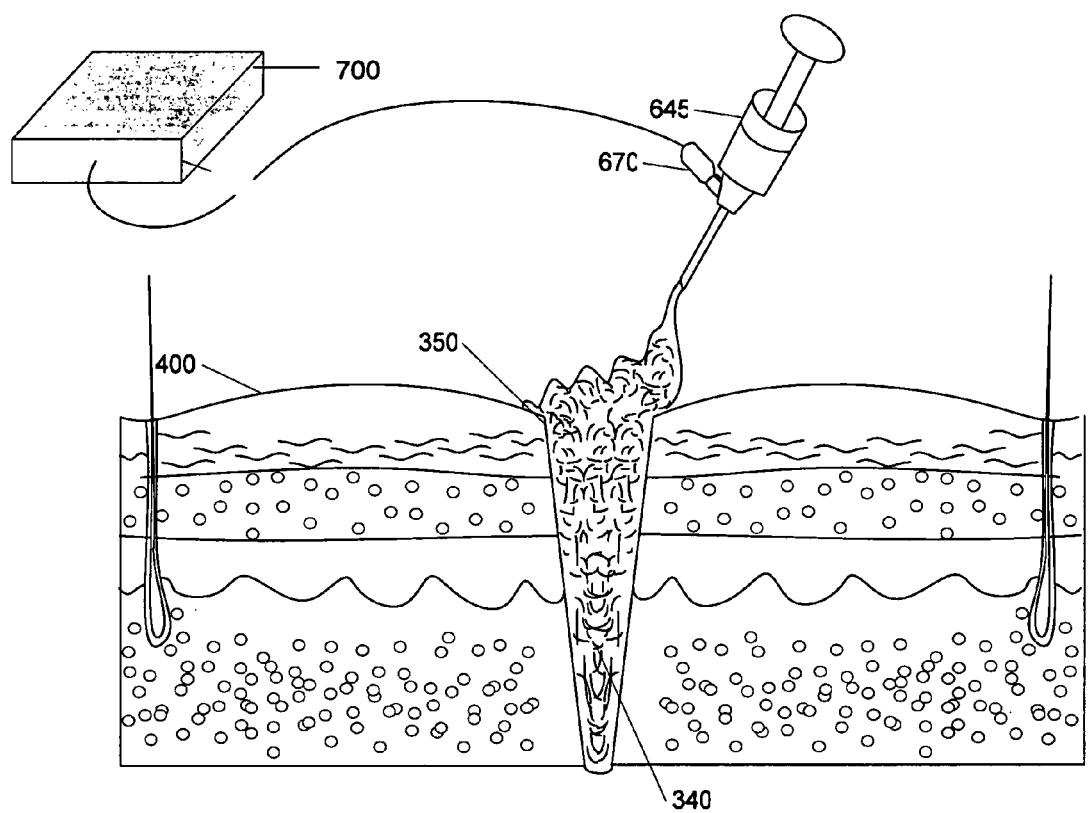
FIG. 10 is a view of an application of the electrosurgical electrolysis interfacing material of the invention upon a wound.
Figure 11:
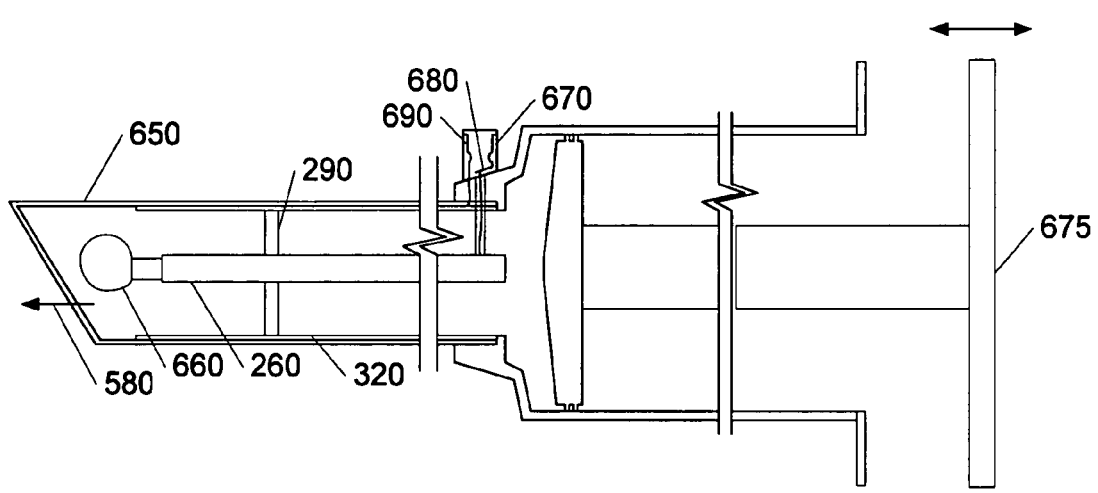
FIG. 11 is a view of a multi-modal electrode electrosurgical electrolysis dispensing probe apparatus of the invention.

FIG. 10 and FIG. 11 illustrate the operation of electrosurgical electrolysis injection application probe apparatus 645, wherein interfacing media or material 340 is a hydrogel including compounds such as calcium carbonate, potassium permanganate, or sodium carbonate which slowly react when subjected to electrosurgical electrolysis. The hydrogel is delivered in the reacting state to wound site 350 and thereafter transdermally closed 400 via suturing. Electromagnetic energy is delivered to the active electrode from electrosurgical generator 700 via cable coupler 670 and conducted to the near distal probe tip. The active electrode is insulated with external insulating sheath 260 to prevent current density depletion prior to reaching the desired location along the electrode. Active and return electrode(s) contacts 680 and 690 provide means to connect conductors to the active and return electrode(s) respectively. Active electrode 660 is positioned and retained by active electrode vane supports 290. Internal return electrode lumen is lined with internal insulating sheath 320 to provide means to achieve the correct current densities in bi-modal (AC/DC) operation to provide active and return electrode specific functions. As syringe plunger 675 is depressed, the interfacing media or material 340 is forced to flow from the lumen tip directing flow 580 toward the treatment site in the reacting state. The reacting interfacing media or material provides a means to deliver the electrolysis products. As will become apparent to those skilled in the art, active and return electrodes 660 and 650 are bi-modal (AC or DC) and can be easily reversed in polarity in the DC condition to provide the benefits of either the anode or cathode products at the treatment site to generate those conditions relevant for the procedure at hand.

Figure 6:
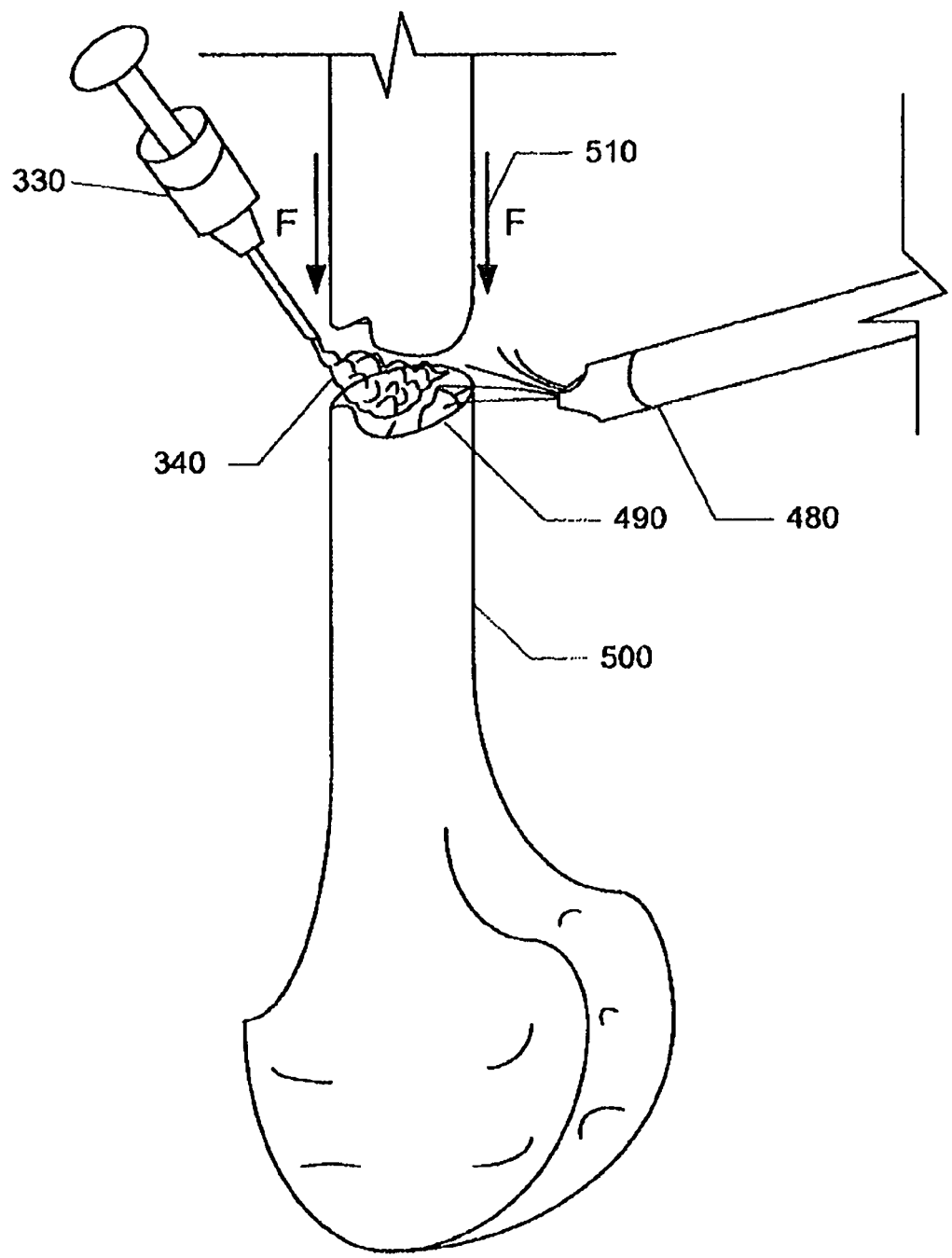
FIG. 6 is a view of a bone welding system utilizing an electrosurgical electrolysis interfacing material of the invention and an electrosurgical electrolysis probe apparatus.
Figure 7:
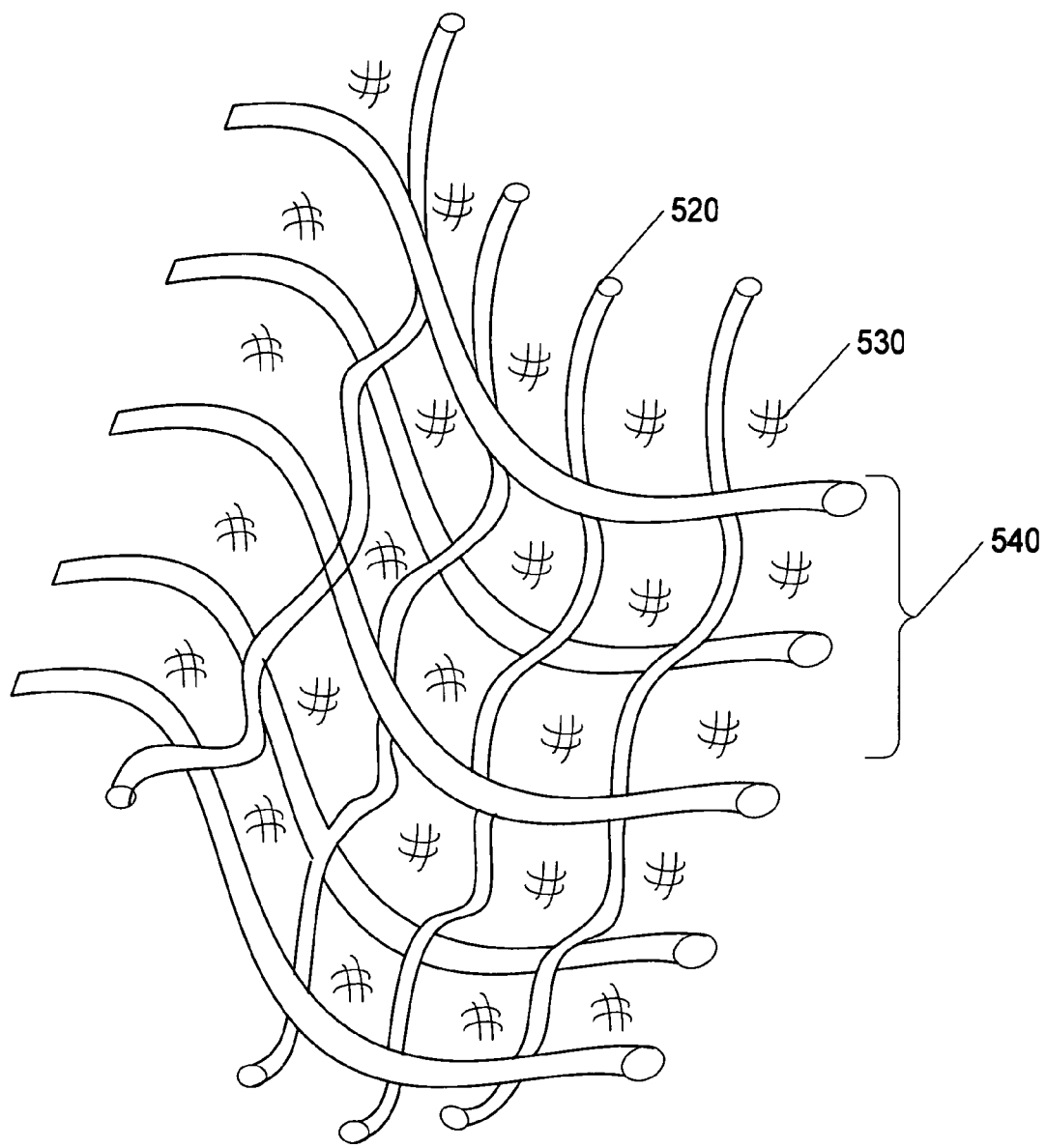
FIG. 7 is a view of an electrosurgical electrolysis scaffold configuration of the invention which provides an alternative configuration of an electrosurgical chamber as depicted in FIG. 2A, FIG. 2B, and FIG. 3.

In other instances as depicted in FIG. 6 and FIG. 7, the interfacing material can be placed within a chamber that is created at a particular therapeutic site application rather than within the electrosurgical probe chamber itself.

FIG. 6 illustrates an embodiment of the methods and devices disclosed herein to aid in the treatment of tissue to induce therapeutic effects. FIG. 6 illustrates that bone tissue can be treated as disclosed in U.S. patent application Ser. No. 09/885,749, via the use of various interfacing media or materials. In this embodiment, interfacing media or materials 340, delivered via syringe 330 or similar device, provides means for bone segments 490 to be physically welded together as disclosed in said application by providing the means to transmit the electrosurgical electrolysis process to the substrate structures of the bone. The interfacing media or materials are activated with an electrosurgical probe configuration as disclosed herein to perform electrosurgical electrolysis of the interfacing media or materials whereby the prepared bone evacuated intersticies can themselves serve as the reaction chamber similar to that described above in FIG. 2A, FIG. 2B, and FIG. 3. The evacuated bone intersticies are acellular and provide a biocompatible electrosurgical electrolysis chamber. Human femur bone 500 is treated with interfacing media or materials 340 and briefly activated with shape memory retractable electrolysis probe apparatus 480 to activate the interfacing media or materials without inducing bone tissue or cellular electrolysis. As femur bone 500 is welded, compressive load 510 is applied to enhance the bone welding procedure and to ensure a good union between the respective segments. The electrosurgical probe is then removed from the treatment site. The character of the interfacing media or materials in this embodiment may be that of a hydrogel or olefin polymer wax preparation as disclosed below, particularly in those instances when a more hydrophobic interfacing media or material is necessary for ease of application. Olefin polymers can be configured to provide a wax-like consistency to such interfacing media or materials in which electrolysis can be achieved.

FIG. 7 details biocompatible interfacing media or materials impregnated composite providing scaffolding or a chamber means to support multiple shape configurations. Chamber strands 520 are comprised of biocompatible materials available from an array of formulations and manufacturers. By way of example, such strands may be constructed of various relative concentrations of a porous copolymer of polyglycolic acid and polylactic acid (for example, D,L [lactide-glycide] PLGA) or other various co-polymers that offer semi-flexible, porous media which may be impregnated with interfacing media or materials 530. Other examples which provide a porous biocompatible structure of various forms that may be impregnated with the interfacing media or materials disclosed herein include collagen networks, demineralized bone matrix, calcium phosphate cements, ceramics like tricalcium phosphate or hydroxyapatite, non-collagenous proteins, bioactive glasses, fabricated porous metals like tantalum, and the like, or various composites thereof. Biocompatible composite manufacture allows that porous formable composites may be used to provide an in situ "shape-to-fit" configuration. The impregnated combination of porous carrier and interfacing media or materials 540 provides means to perform multiple tissue treatments on both hard and soft tissue wherein the mechanical properties of an interfacing media or materials as disclosed herein alone may be insufficient to provide stabilization or fixation of itself. This hybrid or composite provides the chamber as described above in which the electrosurgical electrolysis process occurs. Further, this composite can be utilized to deliver various therapeutic agents to the treatment site. For example, in the case of bone tissue, various osteoinductive or osteogenic agents (osteogenic protein-1, bone morphogenic protein, and the like) can be delivered to the treatment site whereby the interfacing media or materials is conformed to the treatment site and then activated by the electrosurgical methods and devices disclosed herein. Further yet, the scaffolding material that forms the electrosurgical electrolysis chamber can itself exhibit therapeutic properties.

Further, the ability to deliver additional therapeutic agents to the treatment site becomes possible via the activation of the electrosurgical electrolysis process.

Figure 8:
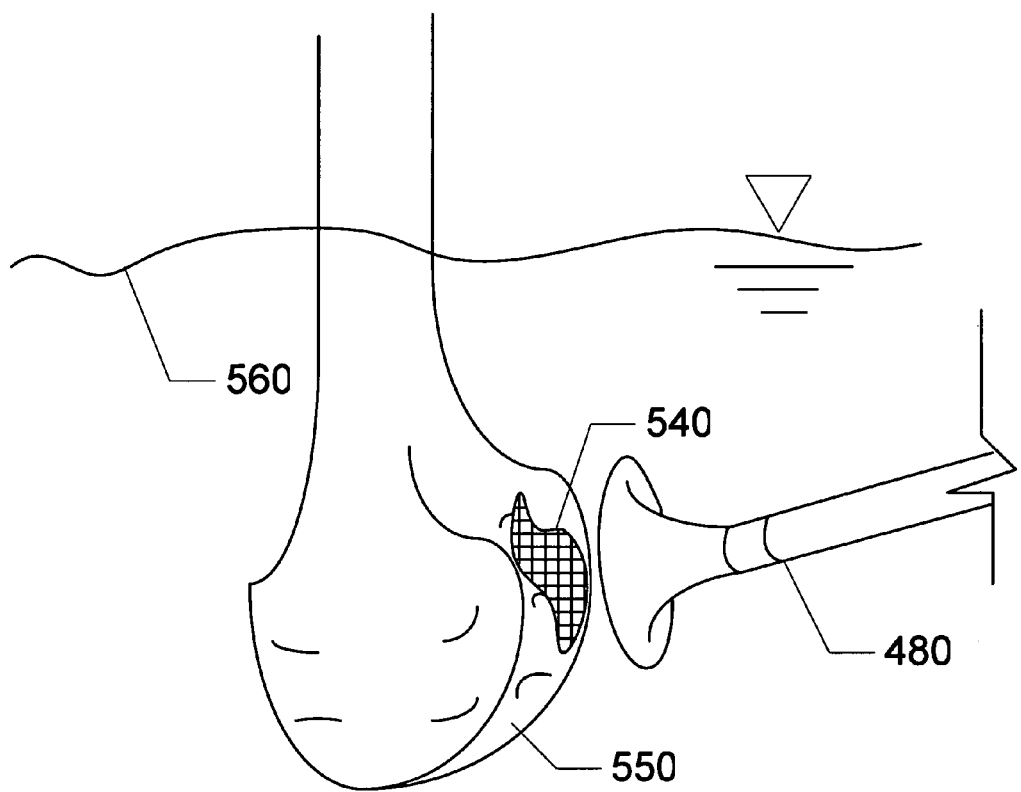
FIG. 8 is a view of an electrosurgical electrolysis trumpet chamber of the invention providing means to perform interfacing material electrolysis for the modification and treatment of cartilage.

FIG. 8 illustrates the operation of flexible retractable transparent polymer trumpet cup electrosurgical probe apparatus 480 with the use of the above embodiment. Flexible retractable transparent polymer trumpet cup electrosurgical probe 480 is extended to provide the largest trumpet exposed electrode area possible. Biocompatible interfacing media or materials 540 are applied to chondral defect 550 and held in place by compaction with the un-activated extended trumpet cup electrode of probe 480. Probe 480 is then centered over interfacing media or materials 540 (or alternatively delivered by the trumpet chamber itself and compressed against the surface of the chondral area, capturing a volumetric portion of intermediary fluid agent 560 for use in the electrolysis activation process. Additionally, probe 480 may be temporarily removed to flush trumpet cup treatment volume repositioned against the desired treatment area and injected with additional therapeutic agents that can take advantage of the altered cellular permeability created by the products of electrosurgical electrolysis. These agents may also be delivered via the trumpet chamber itself or alternatively via the methods disclosed in Patent Cooperation Treaty Application Serial No. PCT/US03/18116, entitled Methods and Devices for Electrosurgery, filed on Jun. 6, 2003. Cycling the method in this way provides means to improve cellular uptake of therapeutic agents over a macro area on the micro-scale as discussed in FIG. 9.

Figure 9:
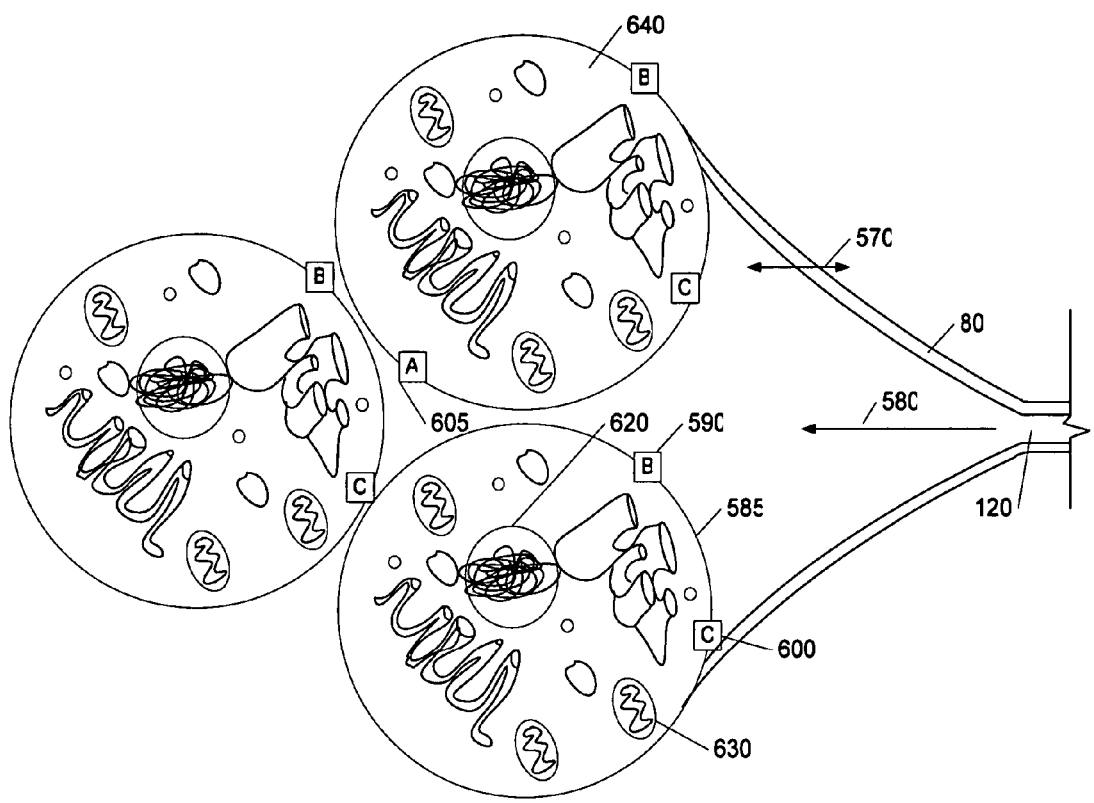
FIG. 9 is a view of non-contact electrosurgical electrolysis tissue modification wherein cellular permeability changes are induced that allow for the subsequent pressure induced uptake of therapeutic agents.

FIG. 9 provides additional detail of the environment created within trumpet cup 80 volumetric treatment areas. Means are provided via flexible injection lumen 120 outlets to direct the flow of therapeutic agents into the volumetric space. Flow 580 of therapeutic agents is directed at cellular based tissue structures interacting with cell membrane 585 or other tissue matrix components. As the products of electrolysis system disclosed suffuse the cellular structures, acid-base shifts which govern permeability regulating pathways 590 across the cell membrane are altered, thereby increasing permeability to intracellular cytoplasm 640. Increased permeability at pathway 590 can be used to infiltrate the cell with therapeutic agents that provide nutrients to cells, increase cell viability, regulate mitochondrial 630 activities and the like. Additionally, treating the tissue cellular structures with a therapeutic agent that first activates DNA specific transport channel 600, as in an mRNA transport channel infiltration of cell nucleus 620, can be achieved. The nucleic impregnation is accomplished via flushing motion 570 and sequential injection of channel activating compounds to trigger preparation of the cell membrane for the reception of the desired cell structure specific therapeutic agent. As the trumpet-cup volume remains static for the treatment cycle, the external free stream conditions may vary significantly with little impact to the controllability of the trumpet-cup volumetric environment. Thus, agents with mild toxicity may now be considered as those skilled in the art will recognize that such mildly toxic agents may both be applied, allowed to interact with said cellular tissue structures, and subsequently during retraction be evacuated via flexible injection lumen 120 to minimize free stream contamination with such mildly toxic agents. Such agents must be of the type with low acute systemic toxicity and sufficiently low allergenic response as to be flushed from the surgical space quickly and sufficiently enough to prevent negative host response. Similar effects can be obtained with, for example, cellular oxygen radical healing response trigger pathway 605.

The configuration of the methods and devices disclosed herein creates an electrosurgical electrolysis-activated treatment composite. The treatment composite is a combination of (1) the electrosurgical electrolysis interfacing media or material, (2) the biocompatible scaffolding or chamber creation materials, which may themselves be therapeutic, and within which the interfacing media or material functions, and (3) the other bioactive elements either within the interfacing media or material or within the biocompatible scaffolding or chamber that aid in specific therapeutic and treatment goals.

In other instances, a more rigid deployment of the interfacing material is preferred in an environment with varying levels of confinement or chamber configuration.

FIG. 10 depicts hydrogel interfacing material 340 applied to open wound closure site 350 by means of electrolysis injection application probe 645 which also includes electrosurgical console power supply input 670 powered by multimodal (AC/DC) electrosurgical console 700. In another embodiment as in FIG. 11, syringe plunger 675 is disposed within a cylinder, for dispensing an electrolytic interfacing material in the direction of interfacing agent pressure flow 580. Electrosurgical console power supply input 670 includes active electrode contact 680 and return electrode contact 690, with input 670 connected to a power supply. Also disclosed is a second multi-mode (AC or DC) active electrode 660 and multi-mode (AC or DC) return electrode 650, with the active electrode 660 disposed in or on insulator sheath 260 and stabilized by means of active electrode vane support 290, all within insulation sheath 320.

Figure 12:
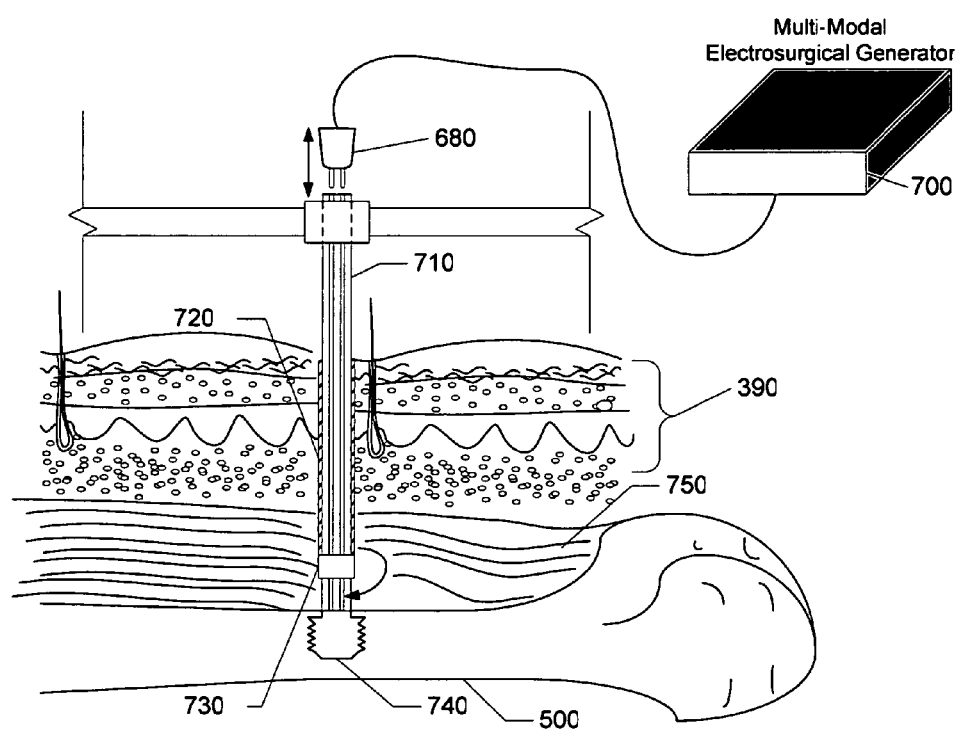
FIG. 12 is a view of a multi-modal electrode electrosurgical electrolysis dispensing apparatus of the invention.

FIG. 12 is another embodiment of the methods and devices disclosed herein whereby an implantable device is utilized to provide both the means to induce electrosurgical electrolysis and the composite as disclosed above. Percutaneous bone pins and fixation devices are utilized wherein percutaneous bone fixation pin 710 is coated with a polymer impregnated with interfacing media or material 720. Bone fixation pin 710 is electrified by electrosurgical console 700 and connected via plug-in adapter 680. Interfacing media or material impregnated polymer 720 is disposed on soft tissue traverse section 390 and muscle section 750 of the bone fixation pin. Proximal to screw fixation point 740, being disposed integrally to shaft section of bone fixation pin, is bone insulating divider 730 a means of preventing tissue electrolysis within the screw fixation bone tissue at the distal portion of the bone fixation pin. Upon activation of the electrified section of bone fixation pin 710 interfacing media or material impregnated polymer 720 exudes liberated products of electrosurgical electrolysis to the soft tissue. This action works against environmental assault via healing wounds at bone fixation pin protrusion points of epidermis 390. While bone fixation pin 710 acts as the active electrode (the return electrode is not shown and is connected remotely as in the mono-polar electrosurgical approach) and conducts electromagnetic energy to the return electrode at sufficiently low current density levels as to prevent tissue electrolysis and subsequent necrosis. Other configurations will become apparent such as use of a screw or anchor as the fixation device, impregnated as discussed with interfacing media or materials, composites, and other therapeutic agents, and then activated by electrosurgical means that are conducted via the screw driver or insertion device for the particular implant device. Further, these implantable devices may themselves be composed of such materials or composites as discussed above.

Figure 13:
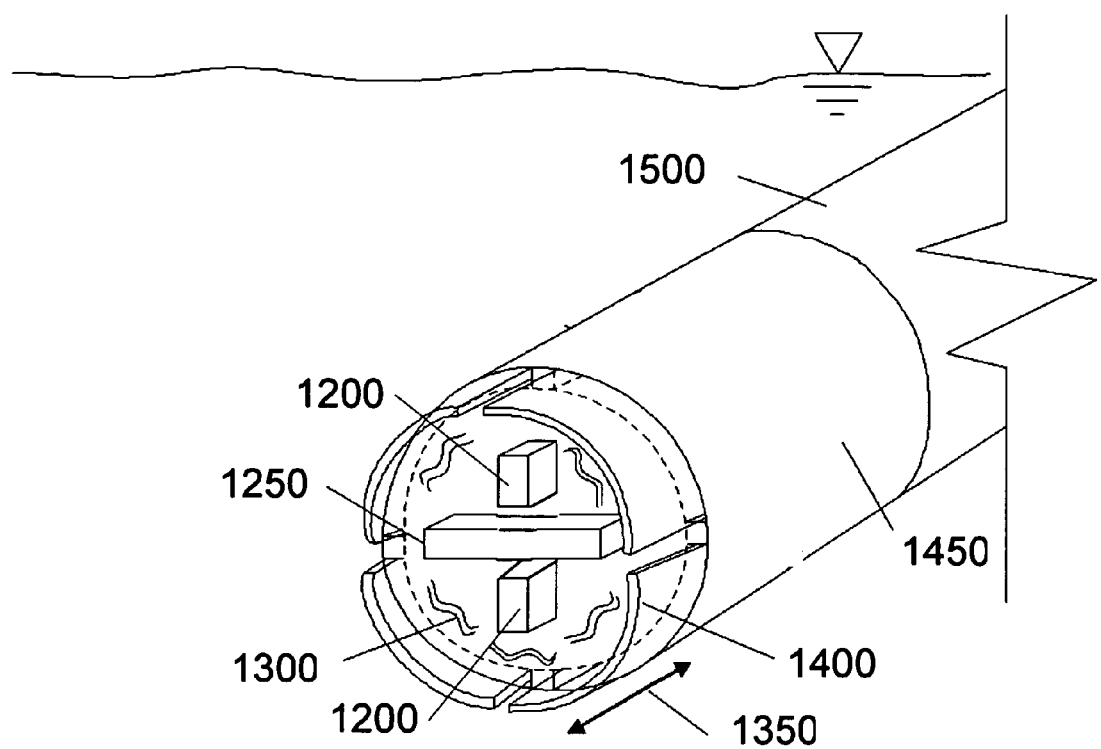
FIG. 13 is an electrosurgical electrolysis probe of the invention with an active electrode and a return electrode disposed within a variable volume and flexible cavity.

FIG. 13 shows yet another embodiment of the invention, an electrolysis probe with both the active and return electrode disposed within a cavity. As shown, lumen support member 1500 is connected to distal insulator support structure 1450, to which is connected a variable volume electrochemical or electrolysis cell spacer 1400. The cell spacer 1400 can translate in a proximal and distal direction as shown by arrow 1350. Within the cell spacer 1400 are disposed return electrodes 1200 and active electrode 1250, with acid-base shift density lines 1300 visible on operation.

Figure 14:
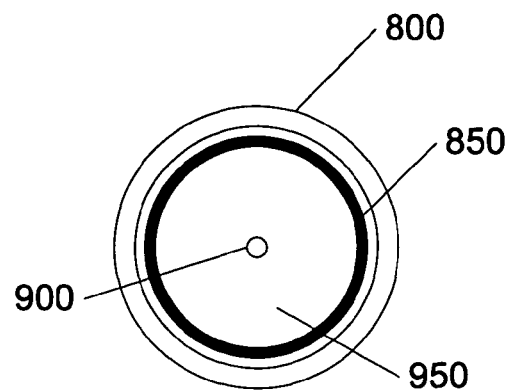
FIG. 14A is a front, head on view of an electrosurgical electrolysis probe of the invention further including a DC driven igniter or glow plug for ignition of oxy-hydrogen combustion.
FIG. 14B is a transverse view of a probe of the invention with a flexible return electrode.
Figure 14:
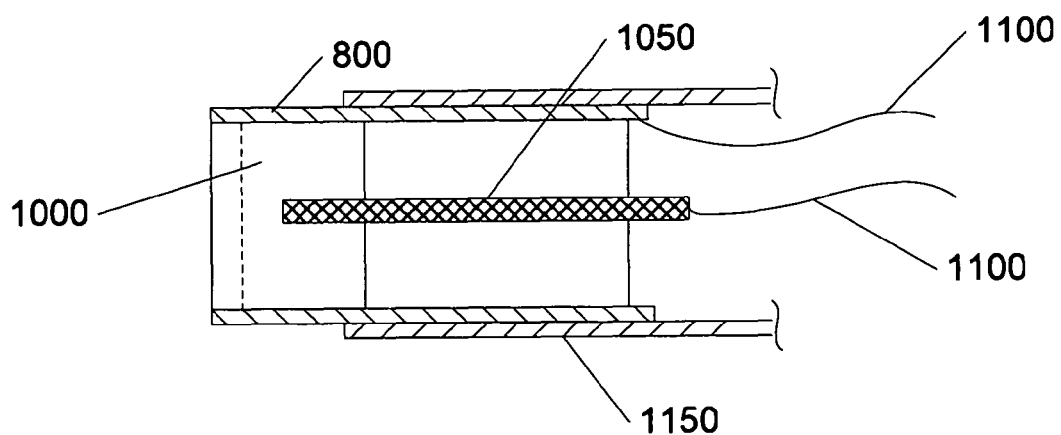

FIG. 14A depicts another embodiment, wherein DC driven igniter or glow plug 900 is provided. In the use of this device, conductively doped polymer electrode 850 and variable volume electrochemical return electrode and cell spacer 800 produce oxygen and hydrogen by means of electrolysis, which gases are optionally ignited by means of igniter 900. As shown, distal support insulator may optionally support igniter 900.

FIG. 14B depicts an embodiment wherein internal surface conductive coating 1000 on the interior of variable volume electrochemical cell spacer and insulator 800 serves as the return electrode, connected to a power supply by means of lead 1100. Active electrolysis electrode 1050 is similarly connected to a power supply by means of electrode lead 1100. The cell spacer and insulator 800 is disposed within probe lumen element 1150, and is preferably movably disposed within probe lumen element 1150.

Figure 15:
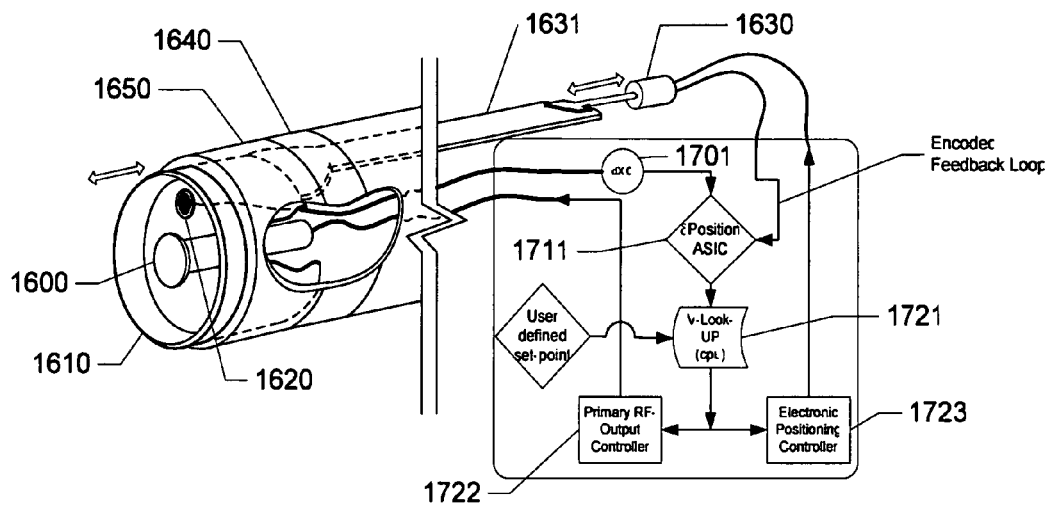
FIG. 15 is a view of a probe of the invention with an adjustable insulating cylindrical sleeve and at least one detector.

FIG. 15 depicts an embodiment of an electrosurgical probe which provides a means for maintaining the optimal spacing of active electrode 1600, disposed distal from the primary lumen 1640 which also acts as a return electrode. Actuating arm 1631, which in turn is driven by electric positioning motor 1630, actuates translatable sheath 1610. Translatable sheath 1610 thus can extend the insulating properties of insulator 1650 beyond the end profile or position of active electrode 1600, providing means to create a variable volume localized chamber when the translatable sheath 1610 is extended. In an alternative embodiment, translatable sheath 1610 can be mechanically actuated, including by means of a thumb control, which may incorporate gears or other means of transferring energy, utilized by the operator. Thus translatable sheath 1610 may, in one embodiment, simply be frictionally engage with a thumb control or other means of movement, may be mechanically actuated, or may be electromechanically actuated. In one embodiment, sensor 1620 provides primary control variable feedback to differential controller 1701, optionally as an analog input. If the input is analog, it may be output via flip-flop A/D conversion to a digital control signal for use by application-specific integrated circuitry logic controller 1711, such as an FPGA, MOSFET, or similar intermediate digital logic gate controlling array. Flash RAM, and additional high level input/output governance, is controlled by CPU 1721, utilizing software governed database lookup techniques, such as those commonly known in C or C++ programming code, to provide dual proportional output via Primary RF Output Controller/Generator 1722; and further and optionally also to Electronic Positioning Controller 1723 for simultaneous balanced positioning of translatable sheath 1610 coupled to matched power setting through controller 1722, providing the primary controlling input to match user set-points according to primary control variable known characteristics correlation to a desired set point. Electrical power may be provided by wires connected to a suitable source of power, which may be one or more sources of power, such as a high voltage source for operation of the active electrode and a lower voltage source for operation of the circuits provided. In the embodiment of FIG. 15, the detector or sensor employed may be any detector or sensor disclosed in Patent Cooperation Treaty Application Serial No. PCT/US03/18116, entitled Methods and Devices for Electrosurgery, filed on Jun. 6, 2003, together with any detection circuit, control circuit or related aspects disclosed therein.

In any of the embodiments discussed herein, a flexible electrode may be employed. The electrode itself may be flexible, and the electrode may further be disposed on a flexible substrate. A preferred embodiment is shown in FIG. 2A, wherein the electrode assembly may be conical or trumpet shaped, so as to conform about and seal an area of tissue to be treated. In one embodiment, the flexible active electrode member of the present invention is a molded polymer or dip layered polymer configured in a semi-conical section wherein the distal end forms a horn section when expanded by a plurality of shape-memory wires, such as may be manufactured of nickel-titanium alloy, heat formed into an arc-shape and distally embedded into the perimeter of the polymer horn section. In order to prevent pressure-induced tearing of the flexible electrode element, a "ball-wire" may be used in which a soldered spherical ball is distally attached to the shape memory wire. The ball end of the wire is then embedded via insert-molding techniques or dip-layering techniques to position the ball within the material of the distal perimeter of the flexible electrode. Such wire embedding techniques facilitate linear force transmission and thereby distribute the strain loads of expanding the flexible electrode element during the expanding step, so that the flexible electrode member is stretched to its final configuration.

In another embodiment of the present invention, the flexible electrode element expands like a centrally expanding fan, with shape-memory alloy wires used in a partially conical section to produce a curved surface that is not self-closing along its distal perimeter.

Each of the shape memory wires can be attached to a cannulated support bushing within the probe handle and supported by a track-guided lumen member that provides the lateral translation necessary to drive the support bushing, shape memory wires, and flexible electrode member into its forward and expanded position. The bushing and lumen members can be attached to an actuator and slide switch disposed on the surface of the probe handle so that the user of the device can selectably position the flexible electrode member at various states of expansion, intra-operatively, as deemed appropriate by observed disease state and treatment requirements.

Other flexible electrode materials may be employed, such as metallic conductive paint, a metallic based conductive adhesive, a plasma vapor deposited metal, a chemical vapor deposited metal, a thin-film metallic leaf, or a conductively doped substrate.

The flexible electrode may be disposed on any of a number of substrates, preferably insulating, including flexible substrates such as a silicone rubber, a polyimide, a fluoro-polymer, a polyester, a polyethylene, a polyurethane, a poly-vinyl chloride, a co-polymer of the foregoing, a tertiary co-polymer of the foregoing or a woven fabric of the foregoing.

The electrosurgical electrolysis chamber can be made of any material, including a material that is transparent or translucent, thereby permitting the operator to view operation of the device. In one embodiment, a bioactive glass can be used, and is further utilized as a biocompatible osteoconductive or bioconductive materials. In this manner, a three-dimensional porous structure is utilized to create treatment chambers of the electrosurgical electrolysis process. The bioactive glass is composed of silica (approximately 45%), calcium oxide (approximately 24.5%), disodium oxide (approximately 24.5%), and pyrophosphate (approximately 6%). These materials can be implanted, bound to collagen or growth factors, fibrin, and other materials and polymers and substances to form a porous matrix within which electrosurgical electrolysis can occur. The matrix provides some compressive strength that is useful in various applications and can be fashioned in many forms including crushed or spherical particles, composite plates, and fibers.

The interfacing media or material may display various characteristics that can be centered on the three components which create the electrosurgical activated treatment composite: (1) interfacing media or material, (2) scaffolding or chamber creation in which the interfacing media or material functions, and (3) other bioactive elements that aid in specific therapeutic and treatment goals. Various configurations of this composite are dependant upon treatment application and the need for relative structural rigidity.

Liquids: The various engineered irrigants as disclosed in U.S. patent application Ser. No. 10/157,651, entitled Biologically Enhanced Irrigants, can serve as the interfacing media. Examples include aqueous salt solutions such as NaCl, carbonated water ($CO_2$), hyaluronan preparations, and the like. An aqueous component is utilized to generate the electrosurgical electrolysis reaction.

Hydrogels: Hydrogels are mainly composed of synthetic polymers or biopolymers such as polysaccharides with varied structures and properties. Substance-holding capacity, nano-structure, chemical structure, and permeability of the hydrogels can be accurately controlled providing numerous options for use of conventional polymer-based hydrogels in this invention. Hydrophilic polymers are useful for a large number of applications in medicine, agriculture, pharmacy, the food industry, cosmetics, construction, and the like and are water soluble at many temperatures and pH. Examples of naturally occurring hydrogels include agar, gelatin, carboxymethylcellulose, hyaluronan, and alginic acid. Natural hydrogel polymers demonstrate both electrolytic properties and biological degradation and thus are very useful for the methods and devices disclosed herein.

Other biodegradable polymers that may be utilized include polyesters, polyanhydrides and polyorthoesters which undergo electrolytic chain cleavage, cross-linked polysaccharide hydrogel polymers, and other ionically cross-linked hydrogels.

Polysaccharides such as calcium alginate or ionically cross-linked cationic polymers such as chitosan, cationic guar, cationic starch, and polyethylene amine can be utilized as these materials are disintegrated in-vivo upon the administration of a chemical trigger material which displaces cross-linking ions.

Other suitable cross-linkable polymers which may be used in the present invention include one or a more of polymers selected from the group consisting of polyhydroxy ethyl methacrylate, polyvinyl alcohol, polyacrylamide, poly (N-vinyl pyrrolidone), polyethylene oxide, hydrolysed polyacrylonitrile, polyacrylic acid, polymethacrylic acid, polyethylene amine, alginic acid, pectinic acid, carboxy methyl cellulose, hyaluronic acid, heparin, heparin sulfate, chitosan, carboxymethyl chitosan, chitin, pullulan, gellan, xanthan, carboxymethyl starch, carboxymethyl dextran, chondroitin sulfate, cationic guar, cationic starch as well as salts and esters thereof. Polymers listed above which are not ionically cross-linkable may be used with polymers which are ionically cross-linkable for certain applications.

Other preferred polymers include one or more of alginic acid, pectinic acid, carboxymethyl cellulose, hyaluronic acid, chitosan, polyvinyl alcohol and salts and esters thereof. Preferred anionic polymers for this application include alginic or pectinic acid; and preferred cationic polymers include chitosan, cationic guar, cationic starch and polyethylene amine.

Other preferred polymers include esters of alginic, pectinic or hyaluronic acid and $C_2$ to $C_4$, polyalkylene glycols, e.g. propylene glycol, as well as blends containing 1 to 99 wt % of alginic, pectinic or hyaluronic acid with 99 to 1 wt % polyacrylic acid, polymethacrylic acid or polyvinylalcohol. Other preferred blends include alginic acid and polyvinylalcohol combinations.

Polyacrylonitrile gels contract when acid environment is applied as that generated by electrolysis of the surrounding media. Such a process only requires 10V of energy and can be useful in many therapeutic applications of this invention.

N-isopropylacrylamide gels demonstrate changing salt concentration like NaCl which in turn changes the gel's volume. Such volume shifts as activated by the electrosurgical means disclosed herein can alter the gel's volume for certain therapeutic applications.

Sol-gels can also be used in the invention. Sol-gel reactions provide a variety of inorganic networks from silicon or metal alkoxide monomer precursors to create materials with desirable properties of hardness, optical transparency, chemical durability, tailored porosity, and thermal resistance that are formed in various shapes as generated in the gel state such as monoliths, films, fibers, and monosized powders. Colloidal suspensions and gelation of the sol forms a network in a liquid phase and react with water. Examples include alkoxysilanes, tetramethoxysilane, tetraethoxysilane, aluminates, titanates, and borates. Three reactions are involved in the sol-gel process, including hydrolysis, alcohol condensation, and water condensation. The sol-gel properties are regulated by pH, temperature, reagent concentrations, and catalyst nature, among others which regulates the respective reactions. The electrosurgical electrolysis process has been shown to be useful in the hydrolysis portion of these reactions as discussed below.

Electrosurgical methods and devices can be used as activators of the sol-gel to allow changes in the sol-gel that allow for specific treatments. Since the byproducts of the sol-gel are water and alcohol, the process is biocompatible. The electrosurgical electrolysis system disclosed herein can be utilized to alter the conductive media to a composition conducive for the sol-gel reactions. For example, varying the acid base mileu, the temperature, the presence of hydrogen and oxygen gas, and the varying salt participation in the electrolysis process all can impart changes in the electrosurgical environment of the sol-gel. Both the acid- and the base-catalyzed mechanism can be used and the process allows aggregation. As the sol-gel particles aggregate or inter knit, a gel forms that is utilized during the treatment. The network can then shrink with further condensation providing fixation of biologic materials. Other esterification and depolymerization reactions can be induced thereafter to strengthen the bonds. Such a process is one way in achieving bone welding or tissue fixation by way of electrosurgical electrolysis.

Further, sol-gels may be employed with the bioactive glasses described above to provide a tissue composite. Tissue bonds to bioactive glass due to formation of a Si-gel layer on the glass. The Si-rich layer acts as a template for a calcium phosphate precipitation which then bonds to the bone. The electrosurgical electrolysis reactions can be used to facilitate, for example, bone welding.

Waxes: Wax preparations in addition to surgical beeswax are very biocompatible and demonstrate properties that can create an interfacing media or materials useful for many applications when subjected to the electrosurgical electrolysis process disclosed herein. For example, intramolecular anodic olefin coupling reactions with an alkoxy substituent on the allylic carbon of an allylsilane moiety have been useful in translating the effects of electrosurgical energy to tissue. These substrates were examined as part of an effort to determine the compatibility of the anodic olefin coupling reactions for the purposes of bone welding. Wax utilized in this fashion can serve at least in part as a piezoelectric polymer transducer.

Other examples include biodegradable polymer ceramic composites with wax-like handling properties, polyethylene glycol/microfibrillar collagen composites, bio-erodible polyorthoesters, and wax matrix layers prepared from a physical mixture of lactose and hydrogenated castor oil. Activation of this class of interfacing material by the electrosurgical means as disclosed herein can allow effective delivery and eludatation of impregnated therapeutic agents.

Solids: Most solids utilized in the methods and devices disclosed herein are used for scaffolding or chamber creating means or treatment enhancing means. In some instances, however, the solids themselves may exhibit electrosurgical electrolysis or become activated by such means. For example, collagen networks can serve as the chamber of the electrosurgical electrolysis process and also be treated by the process (like shrinking). Porous co-polymers of polyglycolic acid and polylactic acid (for example, D,L [lactide-glycide] PLGA) or other various co-polymers offer semi-flexible, porous media which may be impregnated with said interfacing media or materials. Other examples which provide a porous biocompatible structure of various forms that may be impregnated with the interfacing media or materials disclosed herein include collagen networks, demineralized bone matrix, calcium phosphate cements, ceramics like tricalcium phosphate or hydroxyapatite, non-collagenous proteins, bioactive glasses, fabricated porous metals like tantalum, and the like, or various composites thereof. Biocompatible composite manufacture allows that porous formable composites may be used to provide an in situ "shape-to-fit" configuration. The impregnated combination of porous carrier and interfacing material provides means to perform multiple tissue treatments on both hard and soft tissue wherein the mechanical properties of an interfacing material as disclosed herein alone may be insufficient to provide stabilization or fixation means of itself. This hybrid or composite provides the chamber in which the electrosurgical electrolysis process occurs. Further, this composite can be utilized to deliver various therapeutic agents to the treatment site. For example, in the case of bone tissue, various osteoinductive or osteogenic agents (osteogenic protein-1, bone morphogenic protein, and the like) can be delivered to the treatment site within the interfacing media or materials which themselves are within a biocompatible matrix chamber like β-tricalcium phosphate or evacuated porous interstices of the bone itself and are then conformed to the treatment site and then activated by the electrosurgical methods and devices disclosed herein. In this example, the scaffolding material itself exhibits therapeutic properties.

Dye: In various instances, biocompatible dyes may be utilized to distinguish the elements of the interfacing media or material to further guard against unwanted induction of electrolysis of oxy-hydro combustion. Various configurations include compositions including methylene blue tissue dye. Other configurations can be employed that signal the electrosurgical electrolysis reactions such as utilizing an iron(II) agent containing gallic acid entities which are especially suitable as an oxygen indicator of electrosurgical electrolysis.

Surgical procedures inherently involve the introduction of pathogens to the operative field during the procedure. These pathogens can originate for either normal locale colonization, by introduction form the surgeon or other personnel, or form the operating instruments and environment. Standard surgical preparation and draping of the operative field has served as the benchmark of modern surgical site "sterilization". Other methods such as ultraviolet light within the operating room, laminar air flow of the operating room environment, and peri-operative antibiotics have become popular to help decrease the incidence of treatment site infection. However, despite these methods, treatment site infections account for the largest percentage of the morbidity and mortality associated with surgical procedures. Infectious processes significantly impair the healing process at all treatment sites; therefore, it is paramount that both the infectious potential and the healing responses of a treatment site are addressed concurrently to create the best situation for healing.

As a clinical example for further clarification of this disclosure, the use of various aqueous solutions as the interfacing media is readily apparent. For example, articular cartilage contouring can be performed via the methods and devices disclosed. Radio frequency energy that is directed in a non-contact fashion via a water-based media electrolysis reaction can impart articular cartilage shaping. In a clinical study, an electrosurgical probe as depicted in FIG. 2A and FIG. 2B was utilized in a fashion to contain the products of the electrosurgical electrolysis reaction into a local treatment area via the methods and devices disclosed herein as further depicted in FIG. 8. The active electrodes were not allowed to contact the tissue, and by altering the energy configuration, degenerative articular cartilage can be contoured creating a smoother surface beneficial for symptom control. Histological assessments of the cartilage in this mode of treatment do not demonstrate evidence of necrosis at any level, rather a superficial tangential layer that is more congruent and slightly denser with intact cellular structures. In another clinical study, the treated articular cartilage was then allowed to hydrate after such treatment (prior to histological evaluation) and compared to non-treated articular cartilage with similar hydration techniques. The treated articular cartilage demonstrated tissue swelling typical of increased tissue matrix and cellular permeability.

As another clinical example for further clarification of this disclosure, the electrolysis reactions and attendant elements can be used to increase membrane permeability followed by the introduction of therapeutic agents into the cells and/or tissue matrix that otherwise would not be possible to a clinically beneficial degree. For instance, in the clinical example of cartilage described above and as depicted in FIG. 8 and FIG. 9, by creating the electrosurgical electrolysis environment, cellular membrane permeability is increased as the acid-base shift provides alteration of the $Na^+$—$K^+$ pump that maintains cellular and tissue osmotic gradients. The increased permeability induced allow follow-up introduction of therapeutic agents into the treatment site for added efficacy. Hyaluronan is then used to treat the articular cartilage after such electrosurgical treatment. Hyaluronan is a hydrophilic polysaccharide found in all body tissues and fluids and exhibits a wide variety of functions such as lubrication, water homeostasis, filtering effects, regulation of plasma protein distribution, as well as modulating cell proliferation, cell migration, and cellular gene expression (via CD-44 adhesion glycoprotein); anti-inflammatory properties such as prostaglandin, cytokine, and eosinophil regulation as well as accommodating superoxide radicals. These characteristics provide an anabolic effect upon cartilage matrix metabolism; and, when delivered after electrosurgical electrolysis, its efficacy is increased.

As another clinical example for further clarification of this disclosure, hard and soft tissue wounds can be treated with such methods and devices. In the instance of hard tissue, osteomyelitis, for example, can be treated by utilization of the methods and devices disclosed herein. Traditional irrigation and debridement can be followed by treatment with the electrosurgical electrolysis process to further add antimicrobial effects and induce a more robust healing response. The electrosurgical apparatus depicted in FIG. 2A, FIG. 2B, and FIG. 3 can be used as an electrosurgical electrolysis washing or irrigation device whereby the treated tissue is additionally decontaminated and primed for healing. Soft tissue wound sites can be treated as depicted in FIG. 4, FIG. 5A, FIG. 5B, FIG. 10, and FIG. 11 that deliver the beneficial therapeutic effects of this invention either by topical application or by an irrigation type method.

As another clinical example for further clarification of this disclosure, collagen tissue can be treated with such methods and devices as depicted in FIG. 6 and FIG. 7. Controlled shrinkage of collagen fibrils is induced by the low level heat production of the electrosurgical electrolysis reactions induced by electromagnetic energy. The collagen may be part of the tissue to be treated or part of the interfacing composite utilized. In the instances where the collagen is part of the tissue to be treated, wound healing can be augmented and ligament tightening procedures can be safely performed. In the instances where the collagen is part of the interfacing composite, bone welding as disclosed in U.S. patent application Ser. No. 09/885,749 can be performed. Other such uses include collagen gels, meshes, sheets, sponges, fleeces, or composites as delivery vehicles for various antimicrobial or healing augmentation agents (osteoinductive, osteoconductive, osteogenic, growth factors, antibiotics, anti-inflammatories, hormones, and the like). The application of the electrosurgical electrolysis process can mold the composite to its therapeutic position while adding further antimicrobial and healing properties. Further, the collagen fibrils can be used with other scaffolding materials such as ceramic scaffolds like hydroxyapetite or tricalcium phosphates, biomaterials like demineralized bone matrix in various forms including gel, paste, putty, solids, and the like.

As another clinical example for further clarification of this disclosure, implant devices can be treated with such methods and devices as depicted in FIG. 12. In this fashion and as depicted, bone pins or screws can be electrified intermittently in a pulsed fashion. In the case of indwelling devices, this invention can help prevent local pathologic colonization of microbes and also provide a stimulus to the host tissue to seal off the indwelling site. In the case of implanted devices like screws or tissue anchors, this invention can activate the devices upon insertion to stimulate the electrosurgical effects desired prior to withdrawing the insertion devices from the body tissue.

Accordingly, the use of electrosurgical electrolysis and oxy-hydro as described in this invention provides for new and unexpected advantages to the surgeon and patient in improving tissue treatment, providing better control of tissue response and overall efficaciousness of treatments due to improved understanding of physiochemical interactions accurately controlled for such outcomes. Additionally, those skilled in the art will clearly see that embodiments disclosed herein provide means to alter localized tissue chemistry and cellular permeability further allowing improved infiltration capabilities for existing and new therapeutic agents applied directly to tissue structures. Furthermore, knowledge of the actual mechanisms at work in electrosurgery provides new paradigms for treatments heretofore unforeseen such as use of electrolysis products to enhance surgical outcomes. Furthermore, it becomes readily apparent that simple extensions to the inventions disclosed herein can further enhance the objectives of this invention.

The scope of the invention should be determined by the appended claims and their legal equivalents, along with the examples given. The preceding examples can be repeated with similar success by substituting the generically or specifically described elements and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for treating tissue within the body, comprising:
   providing an aqueous electrolyzable interfacing medium adjacent the tissue to be treated;
   providing an active electrode contained within a structure, the active electrode being in fluid contact with the tissue to be treated but spaced by the structure a determinable distance from the tissue to be treated;
   applying sufficient electrical energy to the active electrode to induce electrolysis of the electrolyzable interfacing medium without inducing combustion of the products of electrolysis or formation of a plasma, whereby acid base pairs are generated in the medium adjacent the tissue to provide a therapeutic effect.

2. The method of claim 1, wherein the structure comprises a cavity.

3. The method of claim 1, wherein the structure is a porous structure.

4. A method for treating tissue within the body, comprising:
   providing a probe with a distal end and a proximal end, with at least one active electrode disposed on the distal end;
   positioning the at least one active electrode adjacent the tissue to be treated;
   providing an electrolyzable interfacing medium adjacent the at least one active electrode; and,
   providing sufficient electrical energy to the at least one active electrode to induce electrolysis of the electrolyzable interfacing medium without inducing combustion of the products of electrolysis or formation of a plasma.

5. The method of claim 4 wherein the electrolyzable interfacing medium comprises a hydrogel, a sol-gel, a wax, or a liquid.

6. The method of claim 4 wherein the electrolyzable interfacing medium lubriciously softens in response to electrolysis.

7. The method of claim 4 wherein the electrolyzable interfacing medium comprises an adhesive.

8. The method of claim 4 wherein the electrolyzable interfacing medium comprises a therapeutically effective agent.

9. The method of claim 8 wherein the therapeutically effective agent is an antiseptic, growth factor, or apoptotic agent.

10. The method of claim 4 wherein the electrolyzable interfacing medium effects a change in pH on electrolysis.

11. The method of claim 4 wherein the electrolyzable interfacing medium effects a change in impedance on electrolysis.

12. The method of claim 4 wherein the electrolyzable interfacing medium effects a change in net electrical potential on electrolysis.

13. The method of claim 4 wherein upon electrolysis the electrolyzable interfacing medium forms one or more chemical gradients.

14. The method of claim 4 wherein upon electrolysis the electrolyzable interfacing medium forms a thermal gradient.

15. The method of claim 4 wherein the electrolyzable interfacing medium is provided by disposing within the probe prior to positioning the probe.

16. A method for treating tissue within the body, comprising:
   providing a probe with a distal end and a proximal end, with the distal end comprising a cavity wherein is disposed at least one active electrode;
   positioning the cavity adjacent the tissue to be treated;
   providing an electrolyzable interfacing medium adjacent the at least one active electrode; and,
   providing sufficient electrical energy to the at least one active electrode to induce electrolysis of the electrolyzable interfacing medium without inducing combustion of the products of electrolysis or formation of a plasma.

17. The method of claim 16 wherein the electrolyzable interfacing medium comprises a hydrogel, a sol-gel, a wax, or a liquid.

18. The method of claim 16 wherein the electrolyzable interfacing medium lubriciously softens in response to electrolysis.

19. The method of claim 16 wherein the electrolyzable interfacing medium comprises an adhesive.

20. The method of claim 16 wherein the electrolyzable interfacing medium comprises a therapeutically effective agent.

21. The method of claim 20 wherein the therapeutically effective agent is an antiseptic, growth factor, or apoptotic agent.

22. The method of claim 16 wherein the electrolyzable interfacing medium effects a change in pH on electrolysis.

23. The method of claim 16 wherein the electrolyzable interfacing medium effects a change in impedance on electrolysis.

24. The method of claim 16 wherein the electrolyzable interfacing medium effects a change in net electrical potential on electrolysis.

25. The method of claim 16 wherein upon electrolysis the electrolyzable interfacing medium forms one or more chemical gradients.

26. The method of claim 16 wherein upon electrolysis the electrolyzable interfacing medium forms a thermal gradient.

27. The method of claim 16 wherein the electrolyzable interfacing medium is provided by disposing within the probe prior to positioning the probe.

28. The methods of claim 16 wherein byproducts of electrolysis generated within the cavity are controlled to effect the desired tissue treatment.

29. A method for treating tissue within the body, comprising:
 providing a probe with a distal end and a proximal end, with the distal end comprising a cavity wherein is disposed at least one active electrode;
 positioning the cavity adjacent the tissue to be treated;
 providing an electrolyzable interfacing medium adjacent the at least one active electrode; and,
 providing sufficient electrical energy to the at least one active electrode to induce electrolysis of the electrolyzable interfacing medium without inducing combustion of the products of electrolysis or formation of a plasma; and
 detecting at least one byproduct of electrolysis within the cavity.

30. The method of claim 29 wherein the at step of detecting comprises detecting pH concentration, temperature, conductivity, ion concentrations, gas production, gas consumption, sound, or changes in local pressure.

* * * * *